(12) United States Patent
Bratteli

(10) Patent No.: US 6,733,461 B2
(45) Date of Patent: May 11, 2004

(54) METHODS AND APPARATUS FOR MEASURING ARTERIAL COMPLIANCE, IMPROVING PRESSURE CALIBRATION, AND COMPUTING FLOW FROM PRESSURE DATA

(75) Inventor: Christopher W. Bratteli, Birmingham, AL (US)

(73) Assignee: Hypertension Diagnostics, Inc., Eagan, MN (US)

( * ) Notice: Subject to any disclaimer, the term of this patent is extended or adjusted under 35 U.S.C. 154(b) by 0 days.

(21) Appl. No.: 10/211,857

(22) Filed: Aug. 1, 2002

(65) Prior Publication Data

US 2004/0024324 A1 Feb. 5, 2004

(51) Int. Cl.[7] .............................. A61B 5/02; A61B 5/00; A61B 10/00
(52) U.S. Cl. ...................... 600/490; 600/485; 600/481; 600/300; 128/920
(58) Field of Search ................................ 600/490, 492, 600/493, 494, 495, 496, 481, 483, 485, 486, 300; 128/920, 923

(56) References Cited

U.S. PATENT DOCUMENTS

| 3,651,353 A | 3/1972 | Hugli | 310/8.4 |
|---|---|---|---|
| 4,409,983 A | 10/1983 | Albert | 128/690 |

(List continued on next page.)

FOREIGN PATENT DOCUMENTS

| DE | 4190521 | 3/1990 | H04R/1/46 |
|---|---|---|---|
| EP | 0357275 A1 | 3/1990 | A61B/5/11 |
| WO | WO 87/02233 | 4/1987 | A61B/7/04 |
| WO | WO 92/09232 | 6/1992 | A61B/5/0255 |
| WO | WO 94/05207 | 3/1994 | A61B/7/04 |
| WO | WO 95/06525 | 3/1995 | B06B/1/06 |

OTHER PUBLICATIONS

"Acoustic Contact Sensor", *Apollo Research Corp.*, Model 701010, (1997), 1–5.

"Aging Arteries", *Harvard Heart Letter, 8(2)*, (Oct. 1997), 4 pgs.

"Guide to Modern Piezoelectric Ceramics", Advertising Material from Morgan Matroc, Inc. (undated), 6 pages.

"Harvard Heart Letter", *Harvard Medical School, 7(7)*, (Mar. 1997), 5 pgs.

(List continued on next page.)

*Primary Examiner*—Max F. Hindenburg
*Assistant Examiner*—Navin Natnithithadha
(74) *Attorney, Agent, or Firm*—Lemaire Patent Law Firm, P.L.L.C.; Charles A. Lemaire

(57) ABSTRACT

Methods and apparatus for measuring arterial compliance using combined noninvasive arterial tonometry and cuff oscillometry. Some embodiments include a calibration method using an oscillometric signal to calibrate the pressures of tonometric signals in a contralateral arterial site. The times at which two of the three oscillometric blood pressures (systolic pressure, mean pressure, diastolic pressure) are acquired are identified with times of un-calibrated tonometric pressure waveform. These blood pressures are then used to calibrate the tonometric pressure waveform along (optionally) with adjustments for head pressure. For example, a left brachial arterial cuff oscillometric signal is acquired coincidentally with an un-calibrated right radial arterial pressure tonometric signal. The time points of mean arterial pressure and diastolic pressure are determined from the oscillometric signal and identified with coinciding time points on the tonometric signal to produce a calibration. All pressures are then adjusted by the head pressure between the brachial and radial sites.

55 Claims, 8 Drawing Sheets

U.S. PATENT DOCUMENTS

| | | | |
|---|---|---|---|
| 4,431,873 A | 2/1984 | Dunn et al. | 179/110 A |
| 4,672,976 A | 6/1987 | Kroll | 128/715 |
| 4,784,154 A | 11/1988 | Shirley et al. | 128/715 |
| 4,889,133 A | 12/1989 | Nelson et al. | 128/681 |
| 4,947,859 A | 8/1990 | Brewer et al. | 128/715 |
| 4,949,710 A | 8/1990 | Dorsett et al. | 128/680 |
| 4,993,422 A | 2/1991 | Hon et al. | 128/672 |
| 5,035,247 A | 7/1991 | Heimann | 128/715 |
| 5,054,493 A | 10/1991 | Cohn et al. | 128/672 |
| 5,211,177 A | 5/1993 | Chesney et al. | 128/691 |
| 5,240,007 A | 8/1993 | Pytel et al. | 128/672 |
| 5,241,964 A | 9/1993 | McQuilkin | 128/672 |
| 5,269,312 A | 12/1993 | Kawamura et al. | 128/690 |
| 5,316,004 A | 5/1994 | Chesney et al. | 128/672 |
| 5,337,750 A | 8/1994 | Walloch | 128/680 |
| 5,524,637 A | 6/1996 | Erickson | 128/779 |
| 5,544,651 A | 8/1996 | Wilk | 128/633 |
| 5,551,437 A | 9/1996 | Lotscher | 128/672 |
| 5,551,438 A * | 9/1996 | Moses | 600/485 |
| 5,560,366 A | 10/1996 | Harada et al. | 128/681 |
| 5,577,508 A | 11/1996 | Medero | 128/681 |
| 5,584,298 A | 12/1996 | Kabal | 128/672 |
| 5,590,661 A | 1/1997 | Ohmori et al. | 128/672 |
| 5,592,401 A | 1/1997 | Kramer | 364/550 |
| 5,617,868 A | 4/1997 | Harada et al. | 128/672 |
| 5,623,933 A | 4/1997 | Amano et al. | 128/687 |
| 5,638,823 A | 6/1997 | Akay et al. | 128/691 |
| 5,640,964 A | 6/1997 | Archibald et al. | 128/672 |
| 5,642,733 A | 7/1997 | Archibald et al. | 128/672 |
| 5,647,369 A | 7/1997 | Petrucelli et al. | 128/672 |
| 5,649,542 A | 7/1997 | Archibald et al. | 128/681 |
| 5,671,750 A * | 9/1997 | Shinoda | 600/495 |
| 5,704,362 A | 1/1998 | Hersh et al. | 128/280 |
| 5,752,919 A | 5/1998 | Schrimpf | 600/493 |
| 5,772,620 A | 6/1998 | Szlema et al. | 602/21 |
| 5,845,643 A | 12/1998 | Vergano et al. | 128/877 |
| 5,908,027 A | 6/1999 | Butterfield et al. | 128/672 |
| 6,186,954 B1 * | 2/2001 | Narimatsu | 600/490 |
| 6,554,774 B1 * | 4/2003 | Miele | 600/485 |

OTHER PUBLICATIONS

"Nellcor's N–CAT Continuous Noninvasive Blood Pressure Monitor, Model N–500", Product Publication by Nellcor, Inc., (1991), 9 pages.

"Non–Invasive Arterial Waveform Analysis and Blood Pressure Measurement", Pulse Dynamic Oscillometrics Clinical Information, Pulse Metric, Inc., San Diego, CA, 4.

"Non–Invasive Blood Pressure/Pulse Rate Monitoring and Recording System", Portfolio™ Health Series, 6 pages.

BING, et al., "Reversal of Acetylcholine Effect on Atherosclerotic Coronary Arteries by Estrogen: Pharmacologic Phenomenon of Clinical Importance?", *Journal of the American college of Cardiology*, (Aug. 1992), 3 pages.

BRINTON, et al., "Arterial Compliance by Cuff Sphygmomanometer", *Hypertension, 28(4)*, Application to Hypertension and Early Changes in Subjects at Genetic Risk, (Oct. 1996), 599–603.

BRINTON, et al., "The Development and Validation of a New Non–invasive Method to Evaluate Ventricle Function During Routine Blood Pressure Monitoring", *American Journal of Hypertension, 10(4) Part 2 (Abstract Issue)*, (1997), 2 pages.

COHN, J. N., et al., "Noninvasive Pulse wave Analysis for the early detection of Vascular Disease", *Hypertension, 26*, (Sep., 1995), 503–508.

GLASSER, et al., "Vascular Compliance and Cardiovascular Disease", *AJH, 10(10), Part 1,* (Oct. 1997), 1175–1189.

KLUGER, J., "Beyond Cholesterol", *Time*, (Aug. 4, 1997), 48.

MCVEIGH, et al., "Vascular Abnormalities Associated with Long–term Cigarette Smoking Identified by Arterial Waveform Analysis", *The American Journal of Medicine 102*, (Mar. 1997), 227–231.

RAJKUMAR, et al., "Hormonal Therapy Increases Arterial Compliance in Postmenopausal Women", *JACC, 30(2)*, (Aug. 1997), 350–356.

SIMON, et al., "Detection of Preclinical Atherosclerosis May Optimize the Management of Hypertension", *AJH 10(7) Part 1,* (Jul. 1997), 813–824.

Yoshizawa, et al., "Classical but Effective Techniques for Estimating Cardiovascular Dynamics", *IEEE Engineering in Medicine & Biology Magazine, 16(5)*, (Sep.–Oct. 1997), 106–112.

* cited by examiner (AXIAL SECTION)

NET SHEAR FORCE: $F_{sh}(\ell) = F(\ell + \delta\ell) - F(\ell)$ (LONGITUDINAL SECTION)

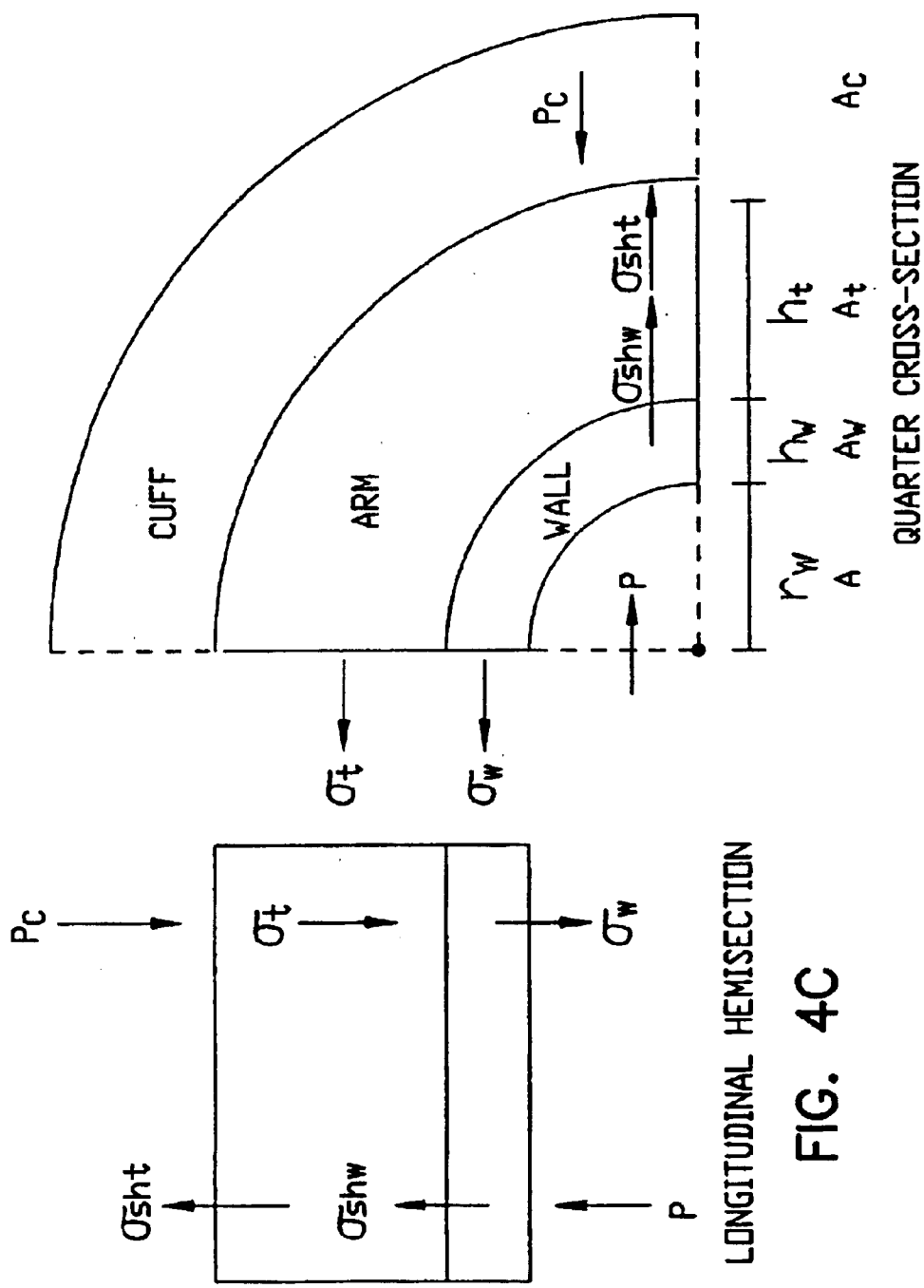

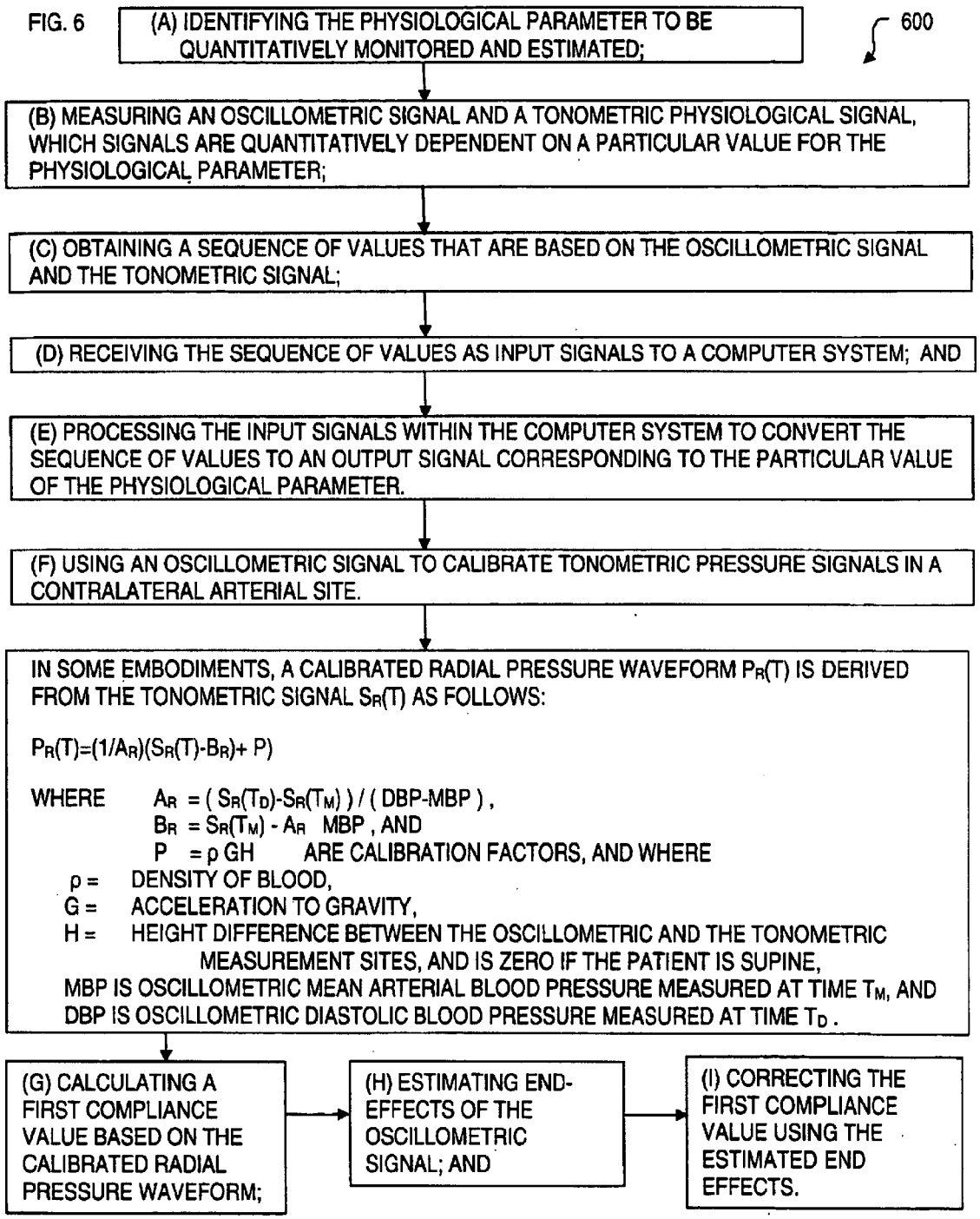

METHODS AND APPARATUS FOR MEASURING ARTERIAL COMPLIANCE, IMPROVING PRESSURE CALIBRATION, AND COMPUTING FLOW FROM PRESSURE DATA

FIELD OF THE INVENTION

This invention relates to the field of medical diagnosis, and more specifically, to a method and apparatus for noninvasive measurement of arterial compliance.

BACKGROUND OF THE INVENTION

High blood pressure and hardening of the arteries can lead to coronary problems. Obtaining various measurements of the vascular system, including compliance of large and small vessels, and systemic resistance, provides physicians with information useful in diagnosing and treating early stages of coronary disease.

U.S. Pat. No. 6,017,313 ("the '313 patent") to Christopher W. Bratteli et al. (incorporated herein by reference) discloses an apparatus and method for blood pressure pulse waveform contour analysis. Methods of processing an arterial blood pressure waveform to extract clinically useful information on the state of the cardiovascular system are disclosed. In order to obtain the parameters of the modified Windkessel model, the diastolic portion of a subject's blood pressure waveform is scanned over a plurality of ranges and the range that produces the best fit of data and lowest error estimates are selected.

U.S. Pat. No. 5,211,177 ("the '177 patent") to Charles F. Chesney et al. (incorporated herein by reference) discloses method and apparatus for measuring properties of the human vasculature using an electrical analog model of vascular impedance. These properties include the compliance of large and small vessels, and systemic resistance. These measurements and others obtained from the model can, in turn, be used to diagnose states of health or disease, and to assess the effectiveness of treatment regimes. For example, see Finkelstein, S. M., Collins, V. R., Cohn, J. N., *Arterial vascular compliance response to vasodilators by Fourier and pulse contour analysis, Hypertension* 1988:12:380–387, the entire disclosure of which is incorporated herein by reference.

U.S. Pat. No. 6,159,166 ("the '166 patent") to Charles F. Chesney et al., and entitled SENSOR AND METHOD FOR SENSING ARTERIAL PULSE PRESSURE (incorporated herein by reference) discloses a method and apparatus useful for tonometric measuring of an arterial pulse pressure waveform. U.S. Pat. No. 6,331,161 to Charles F. Chesney et al., and entitled METHOD AND APPARATUS FOR FABRICATING A PRESSURE-WAVE SENSOR WITH A LEVELING SUPPORT ELEMENT (incorporated herein by reference) discloses a method and apparatus of a sensor useful for tonometric measuring of an arterial pulse pressure waveform. U.S. Pat. No. 6,132,383 to Charles F. Chesney et al., and entitled APPARATUS AND METHOD FOR HOLDING AND POSITIONING AN ARTERIAL PULSE PRESSURE SENSOR (incorporated herein by reference) discloses a method and a wrist brace and sensor holder useful with any of the above sensors for tonometric measuring of an arterial pulse pressure waveform.

U.S. Pat. No. 5,241,966 ("the '966 patent") to Stanley M. Finkelstein; et al. issued Sep. 7, 1993 (incorporated herein by reference) discloses an apparatus for measuring stroke volume/cardiac output that includes a transducer for measuring arterial blood pressure waveform, a digitizer for digitizing the analog signal generated by the transducer and a digital signal processor for determining ejection time and heart rate. Processor circuitry determines cardiac output using the ejection time, heart rate, the body surface area and age of the patient.

Compliance is a fundamental property of any pressure-volume system such as the arteries. In the arteries, reduced compliance has been offered as a mechanism whereby the work load on the heart is increased and myocardial perfusion is decreased, thus leading to cardiac disease. It is also thought that disease of the arteries themselves may be evaluated by measurement of arterial compliance. Therefore, arterial compliance is an important cardiovascular parameter.

What is needed is improved noninvasive measurement of arterial compliance.

SUMMARY OF THE INVENTION

The present invention provides improved noninvasive measurement of arterial compliance using a combination of noninvasive arterial tonometry and noninvasive cuff oscillometry. Described are a number of improved approaches to estimating systemic vascular resistance and/or compliance. In one embodiment, a computer-controlled pneumatic cuff having a sensor coupled to sense pressure and pressure variations in the cuff is used to obtain oscillometric signals (e.g., from an upper arm of a patient), and simultaneously a contact-pressure sensor (e.g., some type of microphone) is used to obtain tonometric signals (e.g., from the contralateral wrist of the patient and, e.g., a transducer placed on the radial artery), and the oscillometric signals and tonometric signals, which are correlated to one another in time, are combined to calibrate one another and/or obtain information about the patient not available conventionally. In some embodiments, the oscillometric measurement is used to calibrate the tonometric measurement.

One aspect of the present invention provides a method to compute arterial compliance from oscillometric data ($2^{nd}$ embodiment listed below). This provides a compliance measurement that is distinct from the compliance measurement described in the '177 patent.

Another aspect of the present invention provides a method for improving pressure calibration from oscillometric data ($1^{st}$ and $3^{rd}$ embodiments listed below). This can be used to improve the above measurement, to improve the '177 patent's described compliance measurement, or to improve almost any measurement that uses arterial pressures.

Yet another aspect of the present invention provides a set of methods for building models that compute flow from pressure data (with or without oscillometric data). This can be used in the same way as the cardiac output model described in the '313 patent (i.e., it can be used to improve the compliance estimate).

The present invention provides a number of improvements or refinements to the approaches to waveform analysis set forth in the '177 and the '313 patents. These improvements include an accurate calibration method and apparatus for using an oscillometric signal to calibrate the pressures of tonometric signals in the contralateral arterial site. These improvements also include a simple uncorrected volume arterial compliance curve that is obtained by plotting relative arterial volume under the cuff against brachial arterial transmural pressure. Further improvements account for a bias (i.e., an overestimation of the in vivo compliance curve for the arterial segment due to shear stresses at the ends of the cuff) by providing a correction for the transmural pressure that is based on stress-strain properties of the upper arm.

In some embodiments, the method of the '313 patent is improved with use of the SVR model of the present invention.

BRIEF DESCRIPTION OF THE DRAWINGS

FIG. 4C is a schematic diagram of the forces on an arterial longitudinal section.

FIG. 4D is a schematic diagram of the forces on an arterial cross section in an arm.

FIG. 6 is a more detailed flowchart of an example process for pulse contour analysis according to the present invention.

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

Figure 1A:
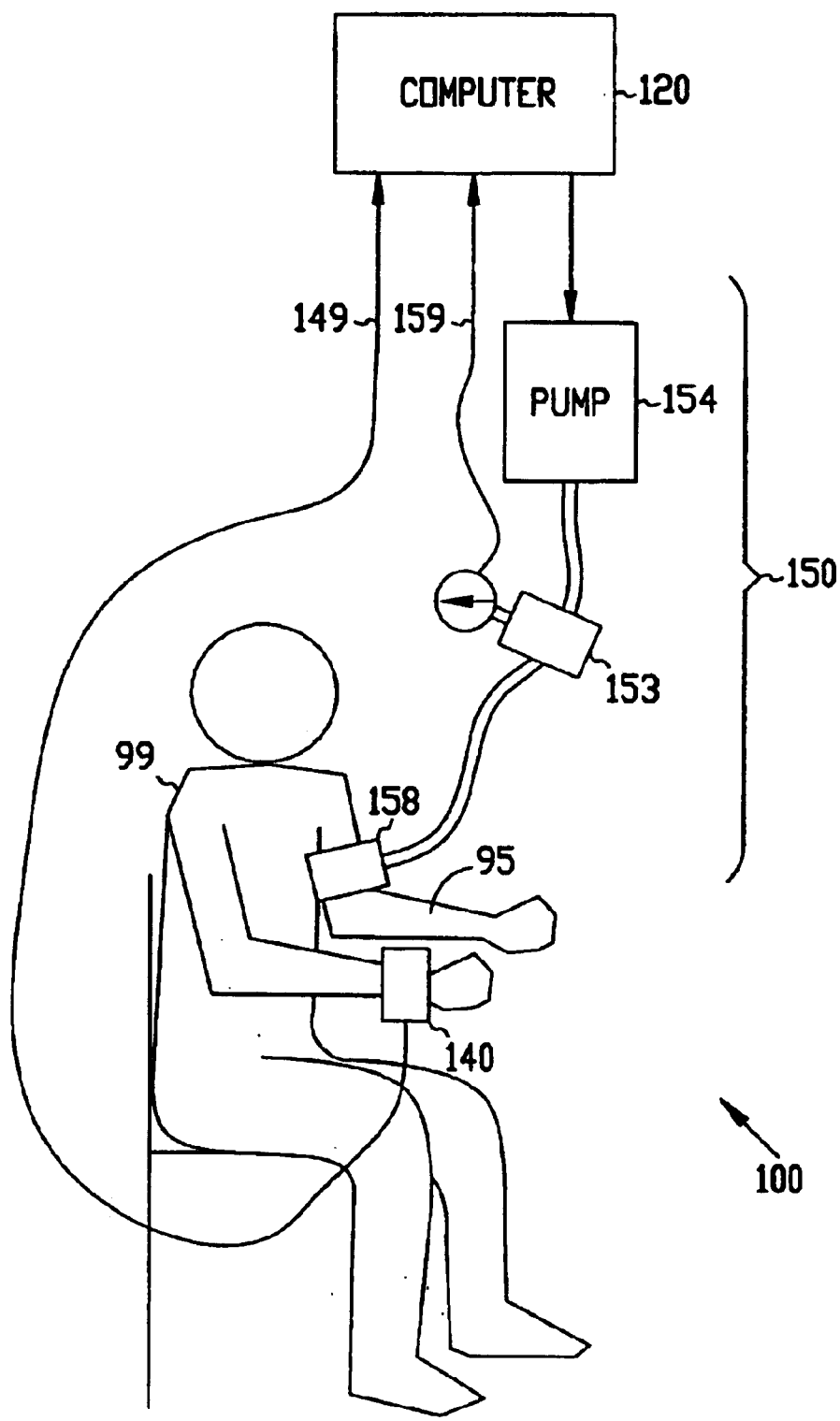
FIG. 1A illustrates an example of a vascular-compliance-determining device 100 according to the present invention.

FIG. 1A illustrates one embodiment of vascular-compliance-determining system 100 according to the present invention. System 100 includes an oscillometric sensor 150 and a tonometric sensor 140, both coupled to computer 120. Tonometric sensor 140 provides tonometric signal 149 to computer 120. In one embodiment, tonometric signal 149 is an analog signal that is sampled and analog-to-digital converted by computer 120 at a fixed sampling rate (e.g., two hundred samples per second) to provide a series of digital values representing the pressure measured at the radial artery of patient 99. Oscillometric sensor 150 includes cuff 158, pressure sensor 153, and pump 154, and generates oscillometric signal 159. Pump 154 is controlled by computer 120, and provides both inflation and deflation functions. In one embodiment, oscillometric signal 159 is an analog signal that is sampled and analog-to-digital converted by computer 120 at a fixed sampling rate (typically fifty samples per second) to provide a series of digital values representing the gauge pressure of the cuff surrounding the brachial artery of patient 99 as the relatively DC pressure on the cuff 158 is varied by pump 154. In other embodiments, non-fixed sampling rates are used.

Figure 1B:
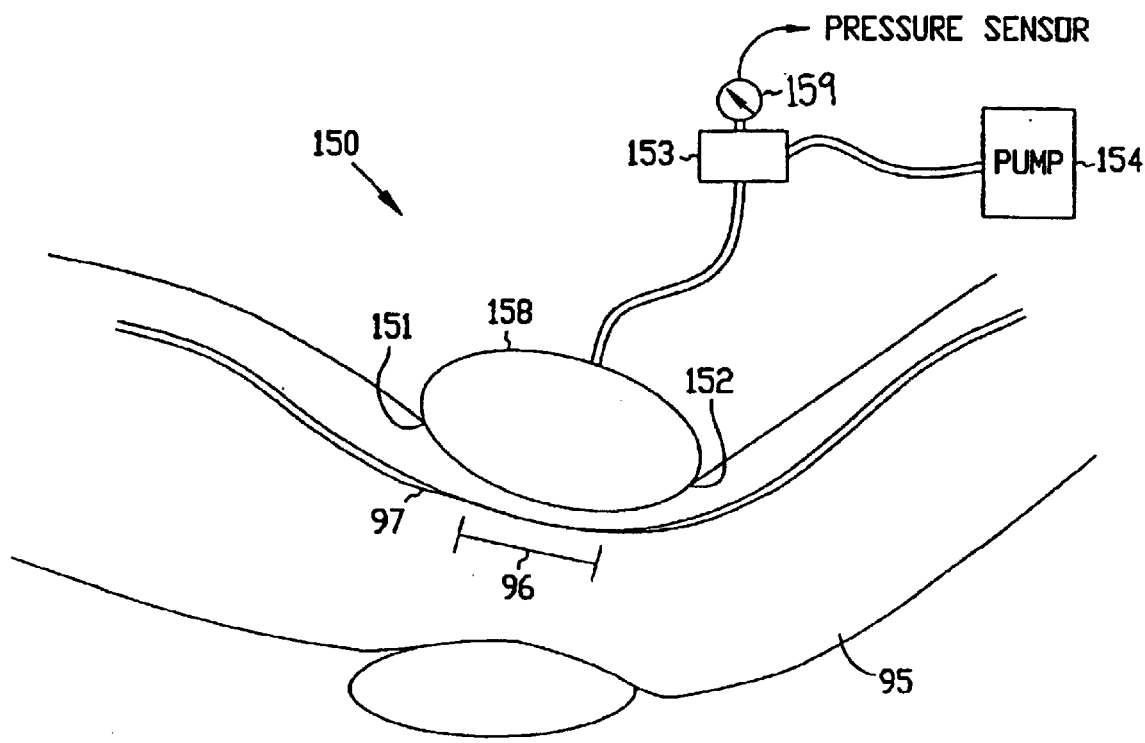
FIG. 1B illustrates schematically details of one embodiment of oscillometric sensor 150.

FIG. 1B illustrates details of one embodiment of oscillometric sensor 150 according to the present invention. Oscillometric sensor 150 includes cuff 158 surrounding brachial artery 96 within the patient's arm 95, pressure sensor 153 coupled to the air line connecting pump 154 to cuff 158, and generates oscillometric signal 159. Artery 96 is shown here in a super-systolic condition, wherein cuff 158 has flattened the artery 96, with a tapered artery portion 97 under proximal cuff end 151, and another tapered portion under the distal cuff end 152. Pump 154 is controlled by computer 120, and provides both inflation (i.e., filling cuff 158 with air) and deflation (i.e., allowing air to exit cuff 158) functions. In one embodiment, inflation is provided by an air pump; Rd deflation is provided by a air-bleed valve, both within pump 150 and controlled by computer 120.

Figure 1C:
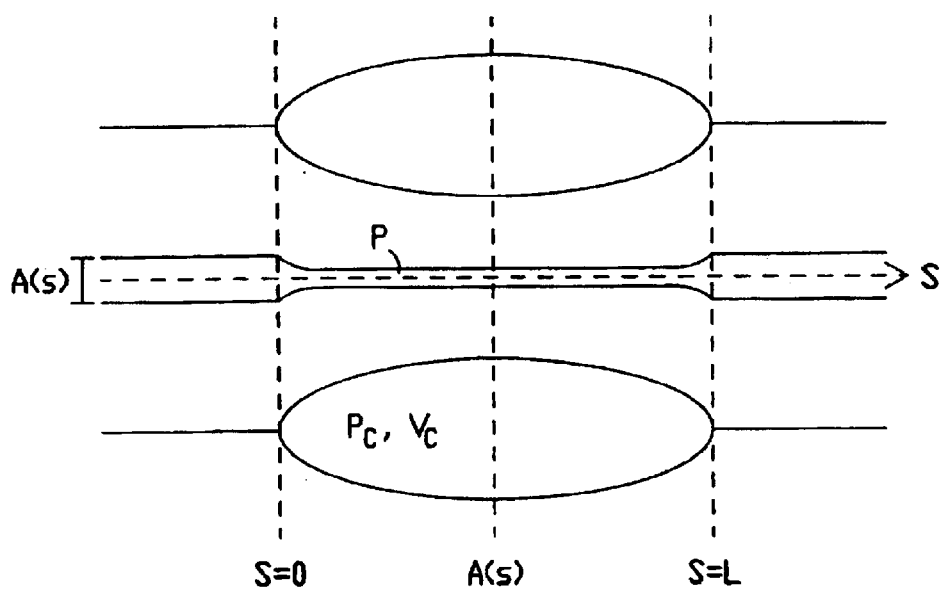
FIG. 1C illustrates schematically details of one embodiment of cuff 158 over an artery.

FIG. 1C illustrates schematically details of one embodiment of cuff 158 over an artery 96.

Figure 2A:
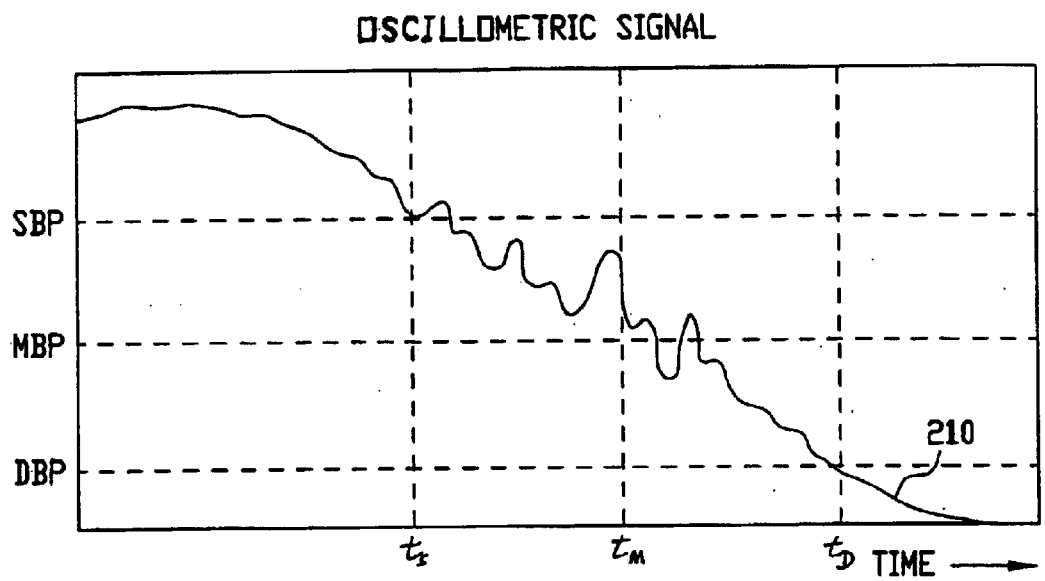
FIG. 2A illustrates an oscillometric arterial blood pressure waveform and points of interest therein.

FIG. 2A illustrates an oscillometric arterial blood pressure waveform 210 of cuff pressure versus time and points of interest therein. At the left edge of the graph, cuff 158 has been inflated to super-systolic pressure, however a small amount of oscillation exists due to shear stresses in the tapered brachial artery under the proximal end of the cuff.

Figure 2B:
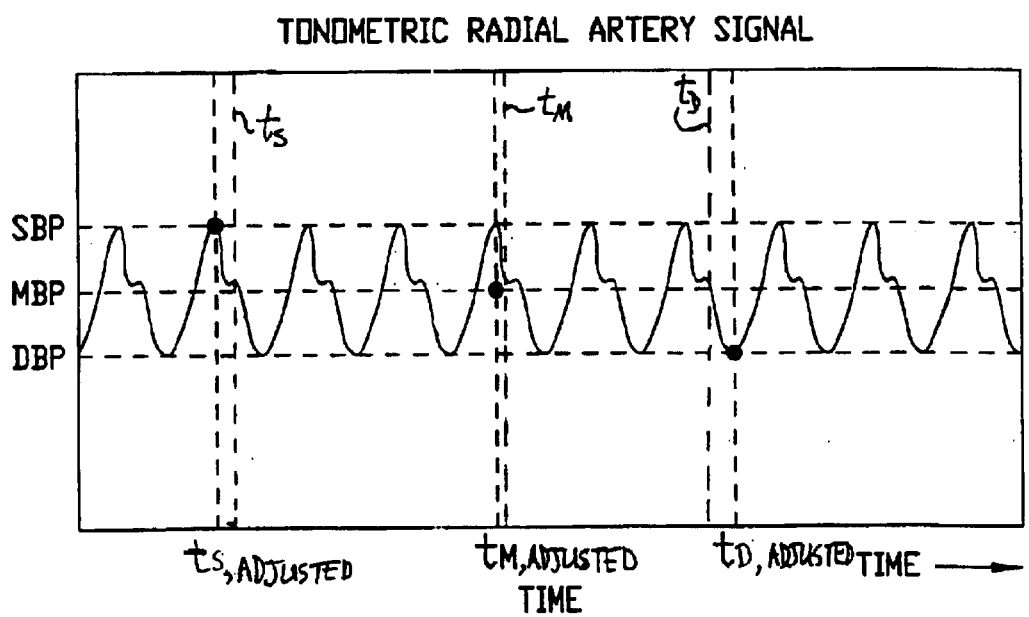
FIG. 2B illustrates a tonometric arterial blood pressure waveform and points of interest therein.

FIG. 2B illustrates a tonometric arterial blood pressure waveform and points of interest therein.

Figure 3:
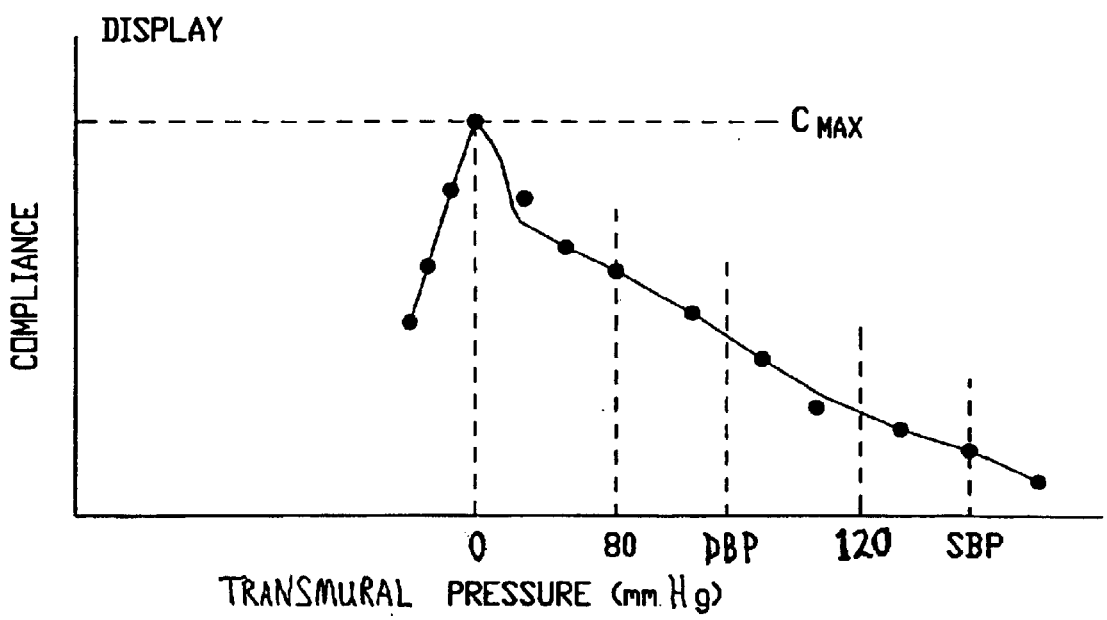
FIG. 3 is an example display of compliance measurements for analysis according to the present invention.

FIG. 3 is an example display of compliance measurements for analysis according to the present invention.

Figure 4B:
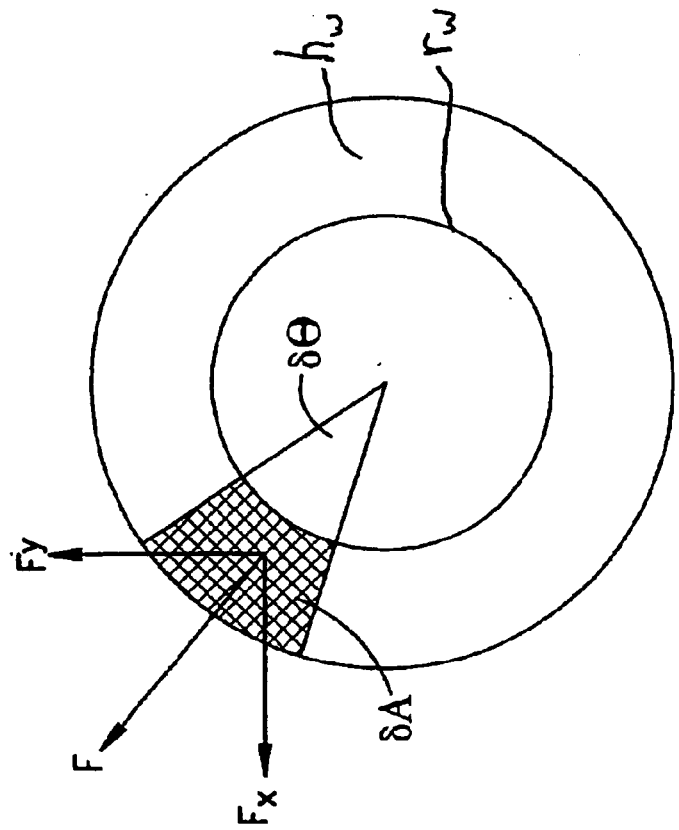
FIG. 4B is a schematic diagram of the forces on an arterial cross section.
Figure 4A:
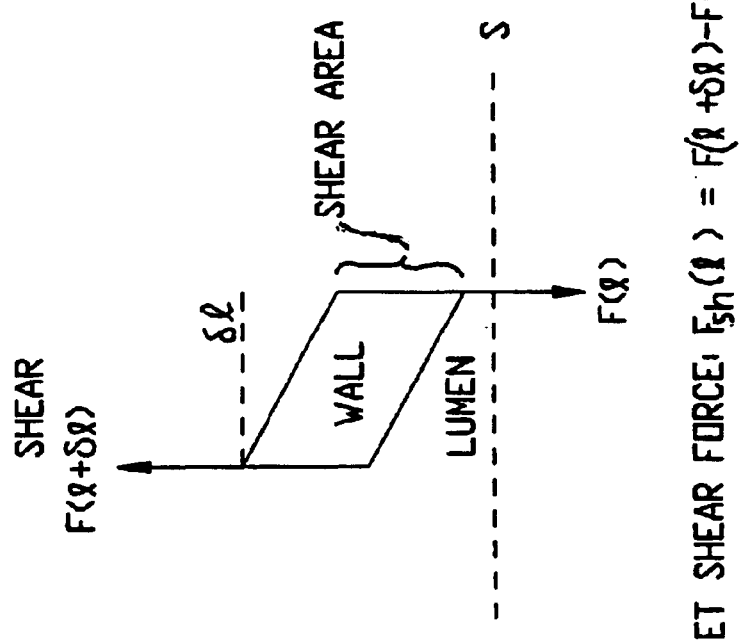
FIG. 4A is a graph of shear force.

FIGS. 4A, 4B, 4C, and 4D show schematically the parameters used in embodiment 3, described below. FIG. 4A is a graph of shear force. FIG. 4B is a schematic diagram of the forces on an axial cross section. FIG. 4C is a schematic diagram of the forces on an axial longitudinal section. FIG. 4D is a schematic diagram of the forces on an axial cross section in an arm.

Figure 5:
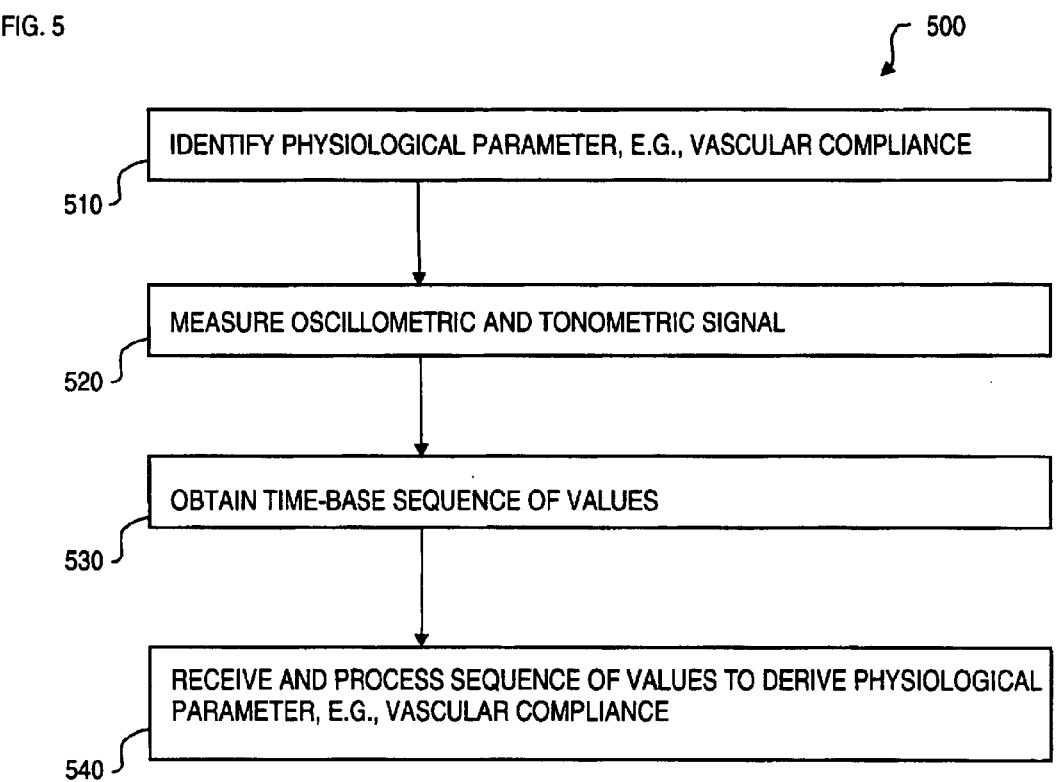
FIG. 5 is an overview of an example process for waveform analysis according to the present invention.

FIG. 5 is an overview of an example process for waveform analysis according to the present invention. Method 500 includes (a) identifying 510 the physiological parameter to be quantitatively monitored and estimated, (b) measuring 520 an oscillometric signal and a tonometric physiological signal, which signals are quantitatively dependent on a particular value for the physiological parameter, (c) obtaining 530 a sequence of values that are based on the oscillometric signal and the tonometric signal, (d) receiving and processing 540 the input signals within the computer system to convert the sequence of values to an output signal corresponding to the particular value of the physiological parameter, e.g., vascular compliance.

FIG. 6 is a more detailed flowchart of an example process for pulse contour analysis according to the present invention. This method includes (a) identifying the physiological parameter to be quantitatively monitored and estimated;

(b) measuring an oscillometric signal and a tonometric physiological signal, which signals are quantitatively dependent on a particular value for the physiological parameter;

(c) obtaining a sequence of values that are based on the oscillometric signal and the tonometric signal;

(d) receiving the sequence of values as input signals to a computer system; and (e) processing the input signals within the computer system to convert the sequence of values to an output signal corresponding to the particular value of the physiological parameter.

(f) using an oscillometric signal to calibrate tonometric pressure signals in a contralateral arterial site.

In some embodiments, a calibrated radial pressure waveform $P_r(t)$ is derived from the tonometric signal $Sr(t)$ as follows:

$$P_r(t)=(1/a_r)(S_r(t)-b_r)+p$$

where $a_r=(S_r(t_D)-S_r(t_M))/(DBP-MBP)$, $b_r=S_r(t_M)-a_r$ MBP, and $p=\rho$ gh are calibration factors, and where
 $\rho$=density of blood,
 g=acceleration to gravity,
 h=height difference between the oscillometric and the tonometric measurement sites, and is zero if the patient is supine,
 MBP is oscillometric mean arterial blood pressure measured at time $t_M$, and
 DBP is oscillometric diastolic blood pressure measured at time $t_D$.

(g) calculating a first compliance value based on the calibrated radial pressure waveform;

(h) estimating end-effects of the oscillometric signal; and (i) correcting the first compliance value using the estimated end effects.

As used herein, arterial compliance is defined as the absolute increase in arterial lumen volume for a given increase in arterial lumen transmural pressure, or Compliance=$dV/dP_{TR}$.

The static pressure-volume relationship in the arterial lumen is the result of a balance of forces. Forces working to reduce lumen size are atmospheric pressure around the arm, tensions in the tissues surrounding the artery, and tensions in the walls of the artery. Forces working to open the artery are lumen pressure, tensions in the arterial wall working to maintain structure and shape, tethering forces between the walls of the artery and the tissues surrounding the artery, and shear forces that occur when the expansion or compression of one part of the artery pulls on another part. In vivo, the pressure wave travels at many meters per second, and so an artery has the appearance of increasing and decreasing simultaneously along its entire length. This, along with the narrow pressure range and relatively flat compliance range that occurs under physiological conditions, means that shear forces play a negligible role. However, when a short segment of artery is compressed underneath a blood pressure cuff, shear stresses occur in the arterial walls beneath both ends of the cuff. The effects of these shear forces are for the portions of the artery away from the cuff to pull open the portions just beneath the cuff ends. Thus, even under complete occlusion by the cuff, when the cuff is far above systolic pressure, pressure pulsations from the heart are able to expand the tapered region beneath the proximal end of the cuff because the systolic pressure is augmented by shear stresses. The result is that oscillometric signals persist at super-systolic cuff pressures. Using a blood pressure cuff to measure arterial compliance thus produces compliance estimates that are too high because they include shear stresses that are not present without the cuff. Without cuff compression, compliance is primarily a function of arterial wall stresses and anatomical dimensions.

Cuff oscillometry is currently a widespread technique for obtaining the values of one, two, or three blood pressure points during the cardiac cycle. The technique is most commonly applied to the brachial artery. In this technique, arterial occlusion is obtained by placing a fluid-filled (usually air-filled) compliant chamber such as a cuff or patch around an artery. The pressure in the fluid is mechanically manipulated and measured. Pressure pulsations in the artery create volume displacements which are captured by the cuff. When the volume of the cuff changes, the pressure of the cuff fluid changes. The pressure is measured with a pressure transducer. As the amount of fluid in the cuff is varied between a point producing complete occlusion of the artery, and a point where the cuff and artery become decoupled, a characteristic oscillometric pressure waveform is recorded from the cuff fluid. At high cuff pressures (near arterial occlusion), the artery is in a region of low compliance with the rigid cuff limiting the distensibility of the artery, and the physiologic pressure pulsations produce low amplitude oscillometric signals. As the transmural pressure in the artery approaches the region of maximal compliance, high-amplitude oscillometric signals are produced. As transmural pressures approach their physiologic values, another low compliance region is reached. At this point, the low pressures in the cuff make the cuff very compliant. The combination of low arterial compliance and high cuff compliance again produces low-amplitude oscillometric signals. Pattern-recognition techniques are then used to estimate one or more of the following: systolic pressure, diastolic pressure, and mean pressure. Mean arterial pressure is usually estimated as equal to the cuff pressure near where the oscillations are a maximum.

Cuff oscillometry has been used to estimate elastic properties of the brachial artery such as compliance (Brinton et al., 1997; Brinton et al., 1996; Chio et al., 1989; Chio et al., 1998; Shimazu et al, 1989; see reference list below). The theoretical basis for this capability is that the necessary volume changes are obtained continuously from the oscillometric signal while pressure changes are obtained by identifying patterns within segments of the signal. Unfortunately, continuous pressures are not obtained. One way this may be overcome is to assume a parametric model for the volume pressure relationship and then fit this model using the few pressures that can be obtained from the cuff. Most recent efforts have been to obtain better arterial pressure estimates from the cuff pressure, and an empirical compliance curve is assumed. See U.S. Pat. No. 5,579,778 issued Dec. 3, 1996, entitled "Method and apparatus for producing thermodilution cardiac output measurements utilizing a neural network" by P. D. Baker et al., and U.S. Pat. No. 5,339,818 issued Aug. 23, 1994, entitled "Method for determining blood pressure utilizing a neural network" by P. D. Baker et al.

The present invention shows how the few known pressure points from the oscillometric signal can be coupled with a tonometric signal to estimate a person's compliance curve at both physiological and sub-physiological pressures. The latter may be used, for instance, to determine the amount of blood-pressure reduction needed in a individual to reduce their compliance to normal levels.

A balance of forces on the artery produces the following relationship {SEE Derivations 3}:

$$P+P_{sh}=P_c+P_{c,ex}+P_t$$

where P is lumen pressure, $P_{sh}$ included all pressures to shear forces, $P_c$ is the cuff pressure exerted on the arterial lumen, $P_{c,ex}$ is the cuff pressure exerted on the tissues outside the lumen, and $P_t$ includes all circumferential stresses. Transmural pressure is defined as $$P_{TR}=P-P_c.$$

Combining these relations one gets $$P_{TR}=P_{c,ex}+P_t-P_{sh}$$

Under in vivo conditions, or with a very long cuff, $P_{sh}=0$. It can be shown that {see Derivation 6}

$$P_{sh}=p_1\ d^2\ A/ds^2+p_2\ 1/A\ (dA/ds)^2$$

where A is lumen cross-sectional area, s is the position along a line through the center of the lumen under the cuff, and $p_1$ and $P_2$ are functions of shear moduli and geometry. The third embodiment proposes estimating $P_{sh}$ to produce a corrected estimate of transmural pressure:

$$P_{TR,c}=P_{TR}+P_{sh}$$

In a First Embodiment of the invention, both oscillometric and tonometric signals are measured (in one embodiment, both signals are measured substantially simultaneously to obtain a series of value-pairs in order to obtain values that are correlated to one another), and a calibration is performed. In one such embodiment, the oscillometric signal is measured by a pressure sensor coupled to a pneumatic cuff whose average (i.e., constant, or DC) pressure is manipulated by the control computer (wherein the pressure sensor measures the time-varying (i.e., AC) portion), and the tonometric signal is obtained by a microphone sensor and/or sensor holder and wrist brace as described in the above mentioned U.S. patent applications Ser. No. 09/045,018, Ser. No. 09/394,301, and Ser. No. 09/045,449 (each of which is incorporated herein by reference). In some embodiments, the tonometric signal is measured at the contralateral radial artery site (e.g., the left wrist) from the cuff measurement site (e.g., the upper right arm). For the Radial Signal (Sr) as measured, $$S_r=a_r P_r+b_r$$

where $P_r$ is radial pressure, and $a_r$ and $b_r$ are calibration constants (multiplicative and additive, respectively), and the corresponding time-varying waveform is $$S_r(t)=a_r P_r(t)+b_r.$$

In some embodiments, two pressure points are needed for calibration. In one such embodiment, MBP (mean arterial blood pressure) and DBP (diastolic blood pressure) are chosen, and respective corresponding times $t_M$ and $t_D$ (shifted to the appropriate time within a cardiac cycle, e.g., $t_D$ is shifted to the nearest pulse minimum) are used:

$$S_r(t_M)=a_r\text{MBP}+b_r$$

$$S_r(t_D)=a_r\text{DBP}+b_r$$

$$a_r=(S_r(t_D)-S_r(t_M))/(\text{DBP}-\text{MBP})$$

$$b_r=S_r(t_M)-a_r\text{MBP}$$

The radial artery is approximately six inches below the brachial artery. This creates a hydrostatic pressure head that can be accommodated by a further pressure head correction factor of $p=\rho$ gh, where ρ=density of blood (=1.03 g/cm³)
g=acceleration to gravity (=980 cm/sec²)
h=6" 15 cm
thus p=1.03 g/cm³ 980 cm/sec² 15 cm=15141 g/cm sec²
11 mm Hg if sitting (or 0 if supine)

and the calibrated radial pressure waveform $P_r(t)$ is derived from the Radial Signal $S_r(t)$ as follows:

$$P_r(t)=(1/a_r)(S_r(t)-b_r)+p$$

In another such embodiment, the two pressure points chosen for calibration are MBP (mean arterial blood pressure) and SBP (systolic blood pressure), and respective corresponding times $t_M$ and $t_S$ are used:

$$S_r(t_M)=a_r\text{MBP}+b_r$$

$$S_r(t_S)=a_r\text{SBP}+b_r$$

$$a_r=(S_r(t_S)-S_r(t_M))/(\text{SBP}-\text{MBP}) \text{ and}$$

$$b_r=S_r(t_M)-a_r\text{MBP}.$$

In yet another such embodiment, the two pressure points chosen for calibration are SBP (systolic blood pressure) and DBP (diastolic blood pressure), and respective corresponding times $t_S$ and $t_D$ are used:

$$S_r(t_S)=a_r\text{SBP}+b_r$$

$$S_r(t_D)=a_r\text{DBP}+b_r$$

$$a_r=(S_r(t_S)-S_r(t_D))/(\text{SBP}-\text{DBP}) \text{ and}$$

$$b_r=S_r(t_D)-a_r\text{DBP}.$$

In a Second Embodiment of the invention, a first compliance value (herein also called "an uncorrected compliance value") is calculated as follows:

$$C_u \triangleq \frac{dV}{dP_{TR}} = \frac{d}{dP_{TR}} \int_0^L A(s)\,ds$$

$$P_{TR} \triangleq P-P_c$$

$$V = V_{TOTAL} - V_c - V_{TISSUE} \Rightarrow \frac{dV}{dP_{TR}} = -\frac{dV_c}{dP_{TR}}$$

In some embodiments, it is assumed that the cuff is filled with an ideal gas. Temperature can be eliminated from the ideal gas state equation by assuming adiabatic conditions. According to other researchers (for example, Shimazu, Kawarada):

$$\Rightarrow \frac{(P_c + P_{ATM})V_c^\delta}{n_c} = \text{constant} = \alpha,$$

$$\delta = 1.4 \Rightarrow V_c = \left(\frac{\alpha n_c}{P_c + P_{ATM}}\right)^{\frac{1}{\delta}} \frac{P_{ATM} V_o}{RT_{ATM}} = n_o$$

(Ideal gas law, before inflation)

$$\frac{P_{ATM} V_o^\delta}{n_o} = \alpha = v_o^{\delta-1} RT_{ATM}$$

$V_0$=residual volume in pump system and hose
R=universal gas constant
=8.314 in SI units
$T_{ATM}$=Ambient temperature
$P_{ATM}$=Ambient pressure The computer system controls a cuff/pump system that inflates and deflates the cuff. To keep track of the amount of air in the cuff ($n_c$), one needs to know the inflation and deflation rates for the cuff/pump system.

$$\left[\frac{dn_c}{dt}\right]_{infl} = f_{infl}(t) \Rightarrow n_c(t) = n_o + \int_o^t f_{infl}(t')dt'$$

(inflation)

$$\left[\frac{dn_c}{dt}\right]_{defl} = f_{defl}(t) \Rightarrow n_c(t) = n_{max} + \int_o^t f_{defl}(t')dt'$$

(deflation)

$$n_{max} = n_o + \int_o^{T_{infl}} f_{infl}(t')dt$$

EXAMPLES $f_{infl}(t)=k \rightarrow n_c(t)=n_o+kt$ (inflation)

$f_{defl}(t)=kn_c \rightarrow n_c(t)=n_o+(n_{max}-n_o)e^{-rt}$ (deflation)

Constant r can be obtained for a particular oscillometric device as $$r = -\frac{1}{t_{.01}} \ln \frac{0.01 n_o}{n_{max} - n_o}, t_{.01}x$$

time to 99% complete deflation.

In some of its embodiments, the Second Embodiment uses a method employing the following procedures:
1. Apply cuff oscillometric system to left upper arm
2. Apply tonometer system to right radial artery.
3. Simultaneously, collect oscillometric and tonometer signals.
4. Using the oscillometric algorithm, identify MBP and SBP from oscillometric signal. These pressure points coincide with time points $t_M$ and $t_S$, respectively.

The process 50 begins with digitizing an analog tonometric blood pressure waveform (52), preferably at 200 Hz, with a 16-bit resolution. According to one example embodiment, waveforms are collected for a thirty (30) second duration. These data are stored in RAM 22 or in storage device 24. In addition to tonometric blood-pressure-waveform data, it is also necessary to obtain oscillometric cuff pressure data, input at port 31, which, in one embodiment, is obtained at the same time as tonometric waveform acquisition in order to calibrate the waveform in terms of pressure in mm Hg.

Next, the data is filtered (54), in some embodiments using an eight (8) pole, 25 Hz low pass Butterworth filter with an attenuation of 6.0206 dB at the corner frequency, for the purpose of marking individual beats. The initial filtering at 25 Hz provides sufficient smoothing of the blood pressure data to enable consistent marking for the upstroke (A), peak (B), and end diastolic point (D) for each beat. These locations are identified without the use of derivatives of the pressure data. In order to identify the dicrotic notch (C) and the left and right scan points bracketing the notch (L-R), termed the near-notch region (NNR), derivatives of the pressure waveforms are utilized. Digital derivatives inherently amplify noise in the data and thus, to minimize the noise in the derivatives of the blood pressure waveforms, the portion of the waveform between systole and end diastole for each beat is further filtered in some embodiments using an eight (8) pole, 15 Hz low pass Butterworth filter with an attenuation of 6.0206 dB at the corner frequency.

After the marks have been identified, the digitized waveform data is converted to pressure in mm-Hg for analysis using a two-point calibration. In one embodiment, the median systolic and median upstroke values are used together with the systolic and diastolic measurements of blood pressure obtained from the oscillometric cuff pressure measurement unit 35 to calibrate the pressure data. In another embodiment the median mean waveform value and the median upstroke waveform value together with the mean pressure and diastolic pressure determined from the oscillometric cuff pressure measurement unit 35 could be utilized to calibrate the data. Using a preferred tonometric method (e.g., as in the '177 patent), capture uncalibrated pressure signals from the radial artery at a sampling rate sufficient to identify the peaks and nadirs of individual pulses. Using this signal, identify the peaks and nadirs of the individual pulses using a preferred algorithm (e.g., as in the '313 patent).

1. Using time points from procedure 4, locate corresponding tonometric signal values shift to the nearest peak (for $t_S$), nadir (for $t_D$), or compute the mean of the current pulse (for $t_M$), and calibrate using the First Embodiment, but exclude pressure head correction factor p.
2. Using tonometric and oscillometric pressures, P and $P_c$, compute transmural pressure $P_{TR}=P-P_c$ at each time point.
3. Using $P_c$ and $n_c$ (see Eqn. $VP_n$ above) compute $V_c$.
4. Numerically differentiate the data pairs ($-V_c$, $P_{TR}$) to obtain $$C = \frac{dV}{dP_{TR}} = -\frac{dV_c}{dP_{TR}}$$

as a function of $P_{TR}$.

5. Plot $C(P_{TR})$ and report C(SBP), C(DBP), C(120), C(80), and pressure at $C_{max}$.

Compliance Range: {C(DBP)} to {C(SBP)}
Compliance Range at Normalized Pressure: {C(80)} to {C(120)}
Mean Compliance:

$$\frac{1}{SBP-DBP}\int_{DBP}^{SBP} C(P)dP$$

For example, with SBP=120, DBP=80→

$$\frac{1}{120-80}\int_{80}^{120} C(P)dP$$

Maximum C: {$C_{max}$}

Third Embodiment—Correction for Shear

P=arterial lumen pressure
$P_c$=cuff pressure
$\sigma_t$=tissue circumferential stress
$\sigma_w$=wall (of artery) circumferential stress
$\sigma_{sht}$=tissue shear stress
$\sigma_{shw}$=wall shear stress
r=lumen radius
$h_w$=wall thickness $h_t$=tissue thickness
$A_x$=cross-sectional areas The following is Derivations 1–6.
Please refer to drawings of FIGS. 4A, 4B, 4C, and 4D.

The present invention addresses estimating the systemic vascular resistance element of the $3^{rd}$-order modified windkessel model. Three different solutions to this problem are presented.

Some Basic Fluid Dynamic Preliminaries for the Present Invention

Two independent state variables are used to determine the properties of an arterial system-pressure and flow. The relationships between these variables are quantities that are frequently of interest when describing a person's arterial system. For example, the ratio of flow to the time rate of pressure change is arterial compliance, the steady-state ratio of mean pressure to mean flow gives vascular resistance, and the pressure rate of change and flow rate of change are related through the inertance. Because blood flows in an axial direction, it is often useful to express flow as the product of cross-sectional area and blood velocity.

Because pressure and flow are both needed to describe system properties, and since it is the unknown dependence between these two quantities that is sought by the present invention for each individual who is assessed, a measurement must be independently made of both quantities. In the $3^{rd}$-order modified windkessel model, as described by Cohn & Finkelstein, the problem of obtaining a flow measurement is simplified by only considering the part of the system where net flow from the heart is zero. Since, in addition, systemic vascular resistance is assumed to be constant throughout the heart cycle, we need only a measure of mean flow, otherwise known as cardiac output. Cohn & Finkelstein obtain an independent measurement of cardiac output using an empirical model that is based upon timing information from the pressure wave, and demographic information about the patient. The present invention provides additional approaches that are used, in various embodiments, to obtain an estimate of cardiac output.

In developing a model for cardiac output for use in the $3^{rd}$-order modified windkessel, there are three goals. First, the present invention is concerned only with prediction and not interpretation. That is, the model may be treated as a black box with any variables found to be useful treated as inputs and with cardiac output as the black box output. Second, the model needs to improve upon a model that attributes the same cardiac output (e.g. 5 liters per minute) to all individuals. Even with such a crude model of cardiac output, we know that the windkessel provides discriminating information about arterial compliance. Therefore, improved models of cardiac output may be considered as methods of fine-tuning the modified windkessel. Finally, the present invention makes use of more of the available information that might be useful. This includes the blood pressure and patient demographic information. The conventional Cohn/Finkelstein cardiac output model (see, e.g., U.S. Pat. No. 5,241,966 and Cohn J. N., Finkelstein S., McVeigh G., Morgan D., LeMay L., Robinson J., Mock J., "Noninvasive pulse wave analysis for the early detection of vascular disease," *Hypertension*. 26(3):503–8, 1995 Sep.) meets these three criteria, and next various embodiments are described using three additional approaches.

Before detailing the models, it is useful to recall a deficiency in the $3^{rd}$-order 4-element modified windkessel model. For mathematical clarity, the lumped electrical analog is usually illustrated, rather than the mechanical analog of the model. This is shown in FIG. 1.

A mass balance through the system leads to the following equations:

$i_0 = i_{C_1} + i_L$      Equation (1):

$i_L = i_{C_2} + i_R$      Equation (2):

$i_{C_1} = C_1 dP_1/dt$      Equation (3):

$i_{C_2} = C_2 dP_2/dt$      Equation (4):

$L di_L/dt = P_2 - P_1$      Equation (5):

$P_2 = R i_R$      Equation (6):

where the i's are flows through respective elements. After some minor algebraic manipulations we obtain the following $3^{rd}$-order ordinary differential equation:

$$Ri_0 = \{1 + (RC_1 + RC_2)D - (RC_1L/R)D^2 - (RC_1L/RRC_2)D^3\} P_2$$      Equation (7):

where D is the differential operator with respect to time. Setting $i_0=0$ (for diastole) and using Laplace transforms we easily obtain an expression for $P_2$ as a function directly of time, and indirectly of $RC_1$, $RC_2$, and L/R. We then use curve-fitting to estimate $RC_1$, $RC_2$, and L/R from a sample of measured $P_2$ data. Herein lies the problem—we are unable to estimate $C_1$, $C_2$, or L without a separate estimate of R.

To obtain an estimate of R, we again use equation (6). Throughout we have assumed that R is constant, so integrating both sides we obtain $\int P_2 dt = R \int i_R dt$. We have $P_2$ data, but we don't know $i_R$, so we rearrange equations (1)–(2) to obtain $i_R = (i_0 - i_{C_1}) - i_{C_2}$. Integrating, we get $\int i_R dt = \int i_0 dt - (\int i_{C_1} dt + \int i_{C_2} dt)$. Substituting equations (3)–(4) we get $\int i_{C_1} dt + \int i_{C_2} dt = \int C_1 dP_1/dt\, dt + \int C_2 dP_2/dt\, dt = C_1 \int dP_1 + C_2 \int dP_2 = C_1(P_1 - P_{1,t=t0}) + C_2(P_2 - P_{2,t=t0})$. Since $P_1$, like $P_2$, is a periodic function at steady state, it reaches nearly the same pressure value at any two points separated by a pulse duration. We get $C_1(P_{1,t=t0+T} - P_{1,t=t0}) + C_2(P_{2,t=t0+T} - P_{2,t=t0}) = 0$, so that finally, $R = \int P_2 dt / \int i_0 dt$,      (8) Equation (8):

where the integrals are over a full cardiac cycle. The reason this expression for R is likely to be useful is that $\int i_0 dt = CO/HR$ = stroke volume.      (9) Equation (9):

Heart rate (HR) we can easily obtain from the pressure wave, so we can choose to estimate either stroke volume, or cardiac output.

The Cohn/Finkelstein model for stroke volume is a direct linear parametric model. Here we offer three additional categories of models—an indirect linear parametric model, an indirect nonlinear nonparametric model, and a direct nonlinear nonparametric model.

Indirect Linear Parametric Model

We call this approach linear parametric because it uses ARMAX (AutoRegressive Moving Average with eXogenous input) models [1]. It is indirect because instead of estimating stroke volume directly, ascending aortic cross-sectional area and blood velocity are modeled and combined to estimate stroke volume.

Two ARMAX models are used, one to compute a transfer function from radial arterial pressure to ascending aortic velocity, another to estimate ascending aortic cross-sectional area from radial arterial pressure. A brief review of ARMAX modeling is next presented.

An ARMAX model for y(t) as a function of x(t) is given by $$y[n]=\Sigma_{p=1,P}a[p]y[n-p]+\Sigma_{q=0,Q}b[q]x[n-q]+w[n]+\Sigma_{r=1,R}c[r]w[n-r]$$

Equation (10):

where w is the unknown error, and the vectors a, b, and c are the model parameters. This equation can be rewritten in matrix form as $$Y=\phi\alpha+W\beta$$

Equation (11):

where the matrix $\phi$ consists of columns of shifted vectors of y and x, $\alpha$ contains the 'a' and 'b' parameters, and $\beta$ contains the 'c' parameters. A common way of obtaining estimates of the a, b, and c parameters is to use an iterative two-step ordinary least squares (OLS) algorithm followed by a generalized least squares (GLS) algorithm until convergence is reached [2].

Taking the Z-transform of the above expression for y[n] and rearranging, we obtain $$y(z)=(B/A)x(z)+(C/A)w(z)$$

Equation (12):

where B is a polynomial in $z^{-1}$ with coefficients 'b', A is a polynomial in $z^{-1}$ with coefficients 'a', and C is a polynomial in $z^{-1}$ with coefficients 'c'. Taking the inverse Z-transform gives $$y[n]=\Sigma_{i=1,N}h_v[n-i]\times[i]+\Sigma_{i=1,N}h_w[n-i]w[i].$$

Equation (13):

Estimating y[n] by its expected values (i.e. neglecting error) gives the desired result $$y[n]=\Sigma_i h_v[n-i]\times[i].$$

Equation (14):

ARMAX modeling is straightforward except for the selection of the proper order (P, Q, R). A common way of comparing models of different orders is with a bias-adjusted maximum likelihood estimate such as AIC. Several candidate models are fit and the one with the lowest AIC is chosen.

Allen & Murray used ARMAX models to predict photoelectric phlethysmographic blood volumes from isovolumic calibrated photoelectric finger pressures [3]. They used a first-order two-parameter autoregressive (ARX) model (P, Q, R)=(1,1,0) with b[0]=0. The ability of these low-order models to predict volumes from pressures was modest, but suggests that reasonable models might be obtainable with only a few parameters. Allen & Murray related finger volumes to finger pressures, while our needs are to relate aortic variables to radial arterial pressure. Thus the transfer functions that we compute implicitly combine a local pressure to velocity (or area) transfer function with an interpositional transfer function (aorta to radial artery).

We obtain stroke volume as $$SV=\int \text{flow}(t)dt=\int A(t)v(t)dt \approx \Sigma t_{n=1,N}A[n]v[n]$$

Equation (15):

where A(t) is ascending aortic cross-sectional area as a function of time, v(t) is ascending aortic blood velocity as a function of time, A[n] and v[n] are the corresponding sampled data values, t is the sampling interval, and N is the number of data points, in a single cardiac cycle. Here the integral is approximated with a simple sum, but any appropriate numerical integration could be used to obtain higher precision (e.g. a high-order Newton-Cotes). A[n] and v[n] are obtained as $$A[n]=\Sigma_i h_A[n-i]P_2[i]$$

Equation (16):

$$v[n]=\Sigma_i h_v[n-i]P_2[i]$$

Equation (17):

where $P_2[n]$ is the sampled pressure at the radial artery. The transfer functions $h_A$ and $h_v$ are obtained using t may be restricted to the family (P, Q, 1).

The following procedure is therefore proposed for any particular patient group of interest:
1. Using a Doppler ultrasound (US) probe, obtain real-time ascending aortic cross-sectional areas and blood velocities while simultaneously collecting radial arterial tonometric pressures. Obtain an oscillometric cuff mean and diastolic blood pressure reading immediately before the collection. Obtain several cardiac cycles of data for each of several human subjects.
2. For each subject, estimate the transfer function parameters (a's, b's, and c's) using the two-step ARMAX algorithm described above and selecting the model with the lowest AIC. Obtain both the pressure to velocity transfer function and the pressure to area transfer functions.
3. Average the transfer function parameters for the several beats and for all individuals.
4. Using the averaged transfer function parameters, compute the two transfer functions ($h_v[n]$, and $h_A[n]$).
5. In all future windkessel analyses, estimate SV using Equations (15), (16), and (17).

Indirect Nonlinear Nonparametric Model

This method is called indirect because, again, area and velocity are estimated from pressure. It is called nonlinear nonparametric because a neural network is used. This method is similar to the indirect linear parametric model, with two main differences. First, we train a neural network rather than an ARMAX model. Second, because a neural network is being used, additional parameters are easily incorporated. Similar to the ARMAX model, we need to decide upon a model order (Q). In addition, we need to decide which additional variables to include. As with the present PulseWave® implementation, we use gender, age, height, and weight. Data are collected with Doppler ultrasound and arterial tonometry as described above. Any network activation type can be used, but for demonstration purposes, we will describe a logistic two-layer multiple-layered perceptron (MLP) model. The number of inputs is equal to 4+Q+1. There are two outputs (velocity and area). The number of nodes between the two middle layers must be high enough to describe the input-output map, but not so high as to make training or prediction computationally impractical. We always use the same number of nodes in both layers. The number of nodes is between one and two times the number of inputs. Training proceeds with cross-validation until leave-one-out cross validation sum of squared residuals reaches a minimum (rather than until actual sum of squared residuals reaches a minimum). It is because we are unconcerned with the parameter values of the neural network that this approach is called "nonparametric".

Any nonlinear parameter estimation algorithm may be used, e.g. conjugate gradients, backpropagation, Newton or quasi-Newton methods. Training stops at minimum leave-one-out cross-validation sum-of-squared residuals. The cross-validation sum-of-squares is also used to compare models of different orders. For each beat, we train the two outputs (v[n] and A[n]) to the corresponding pressure, $P_2[n]$, as well as the previous Q $P_2$ values, $P_2[n-i]$ for i=1 ... Q.

Age, height, weight, and sex are also input. The model can be written as $$(v[n], A[n]) = NN(\text{age, height, weight, sex}, P_2[n], P_2[n-1], \ldots, P_2[n-Q]) \quad \text{Eq. (18)}$$

Therefore the following procedure is used, in one embodiment, for a particular group of interest:
1. Collect data as in the indirect linear parametric model above. Because of the generality of neural network models, it may be necessary to obtain data from 50 to 100 individuals.
2. Using the method described above, train and select a neural network configuration that predicts v[n] and A[n] from $P_2[n]$, age, height, weight, and sex (Equation (18)).
3. In all future windkessel analyses, estimate SV using Equations (15) and (18).

Direct Nonlinear Nonparametric Model

This method is called direct because SV is computed directly. It is called nonlinear nonparametric because a neural network model is employed. This approach is similar to the indirect nonlinear nonparametric model except that the neural network output is SV, and a fixed set of pressure values are used as inputs. The model is expressed in the following way:

$$SV = NN(\text{age, height, weight, sex}, P_2[0], P_2[1], \ldots, P_2[tf]) \quad \text{Equation (19):}$$

Unlike with the indirect nonlinear approach, this approach is dependent upon the start and end times used for the pressure inputs. We use the foot of each beat for the first pressure point. Various end-points can be tried to obtain the lowest prediction error. The spacing between samples can also be adjusted to obtain simpler models with fewer inputs. Training should otherwise proceed as described above for the indirect nonlinear nonparametric model.

The following procedure is used, in one embodiment, for a particular group of interest:
1. Using a Fick dilution method, estimate several cardiac outputs for an individual. Simultaneously, collect tonometric pressure recordings at the radial artery that are calibrated to brachial oscillometric cuff blood pressure estimates.
2. Using the method described above, train and select a neural network configuration that predicts cardiac output from $P_2[n]$, age, height, weight, and sex (Equation (19)).
3. In future windkessel analyses, estimate cardiac output using Equation.(19).

Conclusion

One aspect of the present invention provides a method for computerized calculation of a variable physiological parameter of a patient. The first method includes (a) identifying the physiological parameter to be quantitatively monitored and estimated, (b) measuring an oscillometric signal and a tonometric physiological signal, which signals are quantitatively dependent on a particular value for the physiological parameter, (c) obtaining a sequence of values that are based on the oscillometric signal and the tonometric signal, (d) receiving the sequence of values as input signals to a computer system, and (e) processing the input signals within the computer system to convert the sequence of values to an output signal corresponding to the particular value of the physiological parameter.

In some embodiments, the first method further includes (f) using an oscillometric signal to calibrate tonometric pressure signals in a contralateral arterial site.

In some embodiments, a calibrated radial pressure waveform $P_r(t)$ is derived from the tonometric signal $S_r(t)$ as follows:

$$P_r(t) = (1/a_r)(S_r(t) - b_r) + p)$$

where
$a_r = (S_r(t_D) - S_r(t_M))/(\text{DBP} - \text{MBP})$,
$b_r = S_r(t_M) - a_r \text{MBP}$, and
$p = \rho gh$ are calibration factors, and where
  $\rho$ = density of blood,
  $g$ = acceleration to gravity,
  $h$ = height difference between the oscillometric and the tonometric measurement sites, and is zero if the patient is supine,
  MBP is oscillometric mean arterial blood pressure measured at time $t_M$, and
  DBP is oscillometric diastolic blood pressure measured at time $t_D$.

In some embodiments, the first method further includes (g) calculating a first compliance value based on the calibrated radial pressure waveform, (h) estimating end-effects of the oscillometric signal, and (i) correcting the first compliance value using the estimated end effects.

In some embodiments, the processing function (e) includes estimating a first compliance value using a compliance pressure curve.

Some embodiments of the first method further include (j) using a tonometric signal to calibrate oscillometric pressure signals in a contralateral arterial site.

Some embodiments of the first method further include (h) estimating end-effects of oscillometric sensor apparatus on the oscillometric signal.

Another aspect of the present invention provides a method for computerized calculation of a variable physiological parameter of a patient. This second method includes (a) identifying the physiological parameter to be quantitatively monitored and estimated, (b) coupling at least a first sensor and a second sensor to the patient, the first sensor and the second sensor each being responsive to monitor different time-varying physiological waveforms, which waveforms are quantitatively dependent on a particular value for the physiological parameter, (c) obtaining a time-correlated dual sequence of digital values that are based on the waveforms monitored by the first and second sensors, (d) receiving the sequence of digital values as input signals to a computer system, and (e) processing the input signals within the computer system to convert the time-correlated dual sequence of digital values to an output signal corresponding to a value of the physiological parameter.

In some embodiments of the second method, the physiological parameter is vascular compliance, the first sensor monitors an oscillometric waveform, and the second sensor monitors a tonometric waveform. In some embodiments of the second method, the physiological parameter is vascular compliance, the first sensor monitors an oscillometric waveform derived from oscillometric signals of a brachial artery site, and the second sensor monitors a tonometric waveform derived from tonometric signals of a contralateral radial artery site.

Yet another aspect of the present invention provides a system for computerized calculation of a variable physiological parameter of a patient. The system includes a first and a second sensor. The first sensor measures an oscillometric physiological signal that is quantitatively dependent on a particular value for the physiological parameter. The second sensor measures a tonometric physiological signal that is quantitatively dependent on the particular value for the physiological parameter. A first analog-to-digital converter, operatively coupled to the first sensor, generates a first sequence of digital values that are based on the oscillometric signal. A second analog-to-digital converter, operatively coupled to the second sensor, generates a second sequence of digital values that are based on the tonometric signal. A computer system, operatively coupled to the first and second analog-to-digital converters, processes the first and second sequences of values to generate an output signal corresponding to the particular value of the physiological parameter.

In some embodiments, the first sensor senses the oscillometric signal from one side of a patient, the second sensor senses the tonometric signal from a contralateral arterial site, and the computer uses the oscillometric signal to calibrate tonometric pressure signals in the contralateral arterial site.

In some embodiments, the computer derives a calibrated radial pressure waveform $P_r(t)$ from the tonometric signal $S_r(t)$ as follows:

$$P_r(t)=(1/a_r)(S_r(t)-b_r)+p$$

where $a_r=(S_r(t_D)-S_r(t_M))/(DBP-MBP)$, $b_r=S_r(t_M)-a_r$ MBP, and $p=\rho$ gh are calibration factors, and where $\rho$=density of blood, g=acceleration to gravity, h=height difference between the oscillometric and the tonometric measurement sites, and is zero if the patient is supine, MBP is oscillometric mean arterial blood pressure measured at time $t_M$, &

DBP is oscillometric diastolic blood pressure measured at time $t_D$.

In some embodiments, the computer system further calculates a first compliance value based on the calibrated radial pressure waveform, estimates end-effects of the oscillometric signal, and corrects the first compliance value using the estimated end effects.

In some embodiments, the computer system further estimates a first compliance value using a compliance pressure curve.

In some embodiments, the computer system further uses a tonometric signal to calibrate oscillometric pressure signals in a contralateral arterial site. In some embodiments, the computer system further estimates end-effects of oscillometric sensor apparatus on the oscillometric signal.

REFERENCES

A. Brinton, T. J., Cotter, B., Kailasam, M. T., Brown, D. L., Chio, S. S., O'Connor, D. T., MeMaria, A. N., *American Journal of Cardiology*, 80(3), 323 (1997).

B. Brinton, T. J., Kailasam, M. T., Wu, R. A., Cervenka, J. H., Chio, S. S., Parner, R. J., DeMaria, A. N., O'Connor, D. T., *Hypertension*, 28(4), 599 (1996).

C. Chio, S. S., U.S. Pat. No. 4,880,013 (1989).

D. Chio, S. S., U.S. Pat. No. 5,836,884 (1998).

E. Shimazu, H., Kawarada, A., Ito, H., *Med. & Biol. Eng. & Comnut.*, 27, 477 (1989).

Another aspect of the invention is to improve the accuracy of the estimate of stroke volume using one of three methods. A first method includes measuring a relevant population of persons to determine empirically the $h_A$ and $h_v$ parameters for Equations 16 and 17 respectively, and then using Equations 16 and 17 to derive arterial cross section area A[n] and velocity v[n] respectively. These A[n] and v[n] parameters are then input into Equation 15 to determine an improved estimate of stroke volume. A second method further obtains age, height, weight and sex information for each person in the population used to obtain data to empirically obtain weighting factors, and Equation 18 is then used to obtain the A[n] and v[n] parameters, which are then input into Equation 15 to determine an improved estimate of stroke volume. A third method also obtains age, height, weight and sex information for each person in the population used to obtain data to empirically obtain weighting factors, and Equation 19 is then used to directly obtain an improved estimate of stroke volume. These improved estimates of stroke volume are then used in the methods described above to obtain improved estimates of compliance values.

On the following pages are explanations of the derivations 1–6 described above.

The following is Derivation 1:

Please refer to drawings of FIGS. 4A and 4B.

Here we derive a general expression for a shear force.

$$\delta A = \frac{\delta \theta}{2\pi}\pi((r+h^2)-r^2) = \frac{1}{2}\delta\theta h(h+2r)$$

$$F_{shx} = \int_0^{\pi/2} \sigma_{shx}\delta A_x \cos\theta = \frac{1}{2}\sigma_{shx}h_x(h_x+2r_x)$$

The following is Derivation 2:

Using Derivation 1, we derive expressioms for the rate of change of shear force along the length of the artery. We do so for both the wall and tissue layers. We also define the geometric coefficients, $\Psi$.

$$\frac{dF_{shx}}{dl} = \frac{1}{2}\left\{\sigma_{shx}\left(h_x\left(\frac{dh_x}{dl}+2\frac{dr_x}{dl}\right)+\frac{dh_x}{dl}(h_x+2r_x)\right)+\right.$$

$$\left.\frac{d\sigma_{shx}}{dl}h_x(h_x+2r_x)\right\}$$

$$\sigma_{shx} \stackrel{\Delta}{=} \mu_x \frac{dr_x}{dl}$$

$$\frac{dh_x}{dl} = \frac{dh_x}{dr}\frac{dr}{dl}$$

$$\Rightarrow \frac{dF_{shx}}{dl} = \mu_x\left\{\left(\frac{dr_x}{dl}\right)^2\left(\frac{dh_x}{dr_x}(h_x+r_x)+h_x\right)+\frac{1}{2}\frac{d^2r_x}{dl^2}h_x(h_x+2r_x)\right\}$$

$$\frac{dr_x}{dl} = \left(1+\frac{dh_w}{dr_w}\right)\frac{dr_w}{dl}$$

$$\frac{d^2r_x}{dl^2} = \left(1+\frac{dh_w}{dr_w}\right)\frac{d^2r_w}{dl^2}+\left(\frac{dr_w}{dl}\right)^2\frac{d^2h_w}{dr_w^2}$$

$$\frac{dh_x}{dr_x} = \frac{dh_x}{dr_w}\left(\frac{dr_x}{dr_w}\right)^{-1} = \frac{dh_x}{dr_w}\frac{1}{1+\frac{dh_w}{dr_w}}$$

$$\frac{dF_{shx}}{dl} = \mu_x\left\{\left(\left(1+\frac{dh_w}{dr_w}\right)\frac{dr_w}{dl}\right)^2\left(\frac{dh_x}{dr_x}(h_x+r_x)+h_x\right)+\right.$$

$$\frac{1}{2}\left(\left(1+\frac{dh_w}{dr_w}\right)\frac{d^2r_w}{dl^2}+\left(\frac{dr_w}{dl}\right)^2\frac{d^2h_w}{dr_w^2}\right)h_x(h_x+2r_x)\right\}$$

$$= \mu_x\left\{\left(\frac{dr_w}{dl}\right)^2\left[\left(1+\frac{dh_w}{dr_w}\right)\left(\frac{dh_x}{dr_w}(h_x+h_w+r_w)+\right.\right.\right.$$

$$\left.\left.h_x\left(1+\frac{dh_w}{dr_w}\right)\right)+\left(\frac{h_x}{2}\frac{d^2h_w}{dr_w^2}\right)(h_x+2(h_w+r_w))\right]+$$

-continued $$\left(\frac{h_x}{2}\frac{d^2 r_w}{dl^2}\right)\left[\left(1+\frac{dh_w}{dr_w}\right)(h_x+2(h_w+r_w))\right]\}$$

$$\frac{1}{r_w}\frac{dF_{shx}}{dl}=\mu_x\left\{\left(\frac{dr_w}{dl}\right)^2\Psi_{x1}+\left(\frac{r_w}{2}\frac{d^2 r_w}{dl^2}\right)\Psi_{x2}\right\}$$

$$\Psi_{t1}\triangleq\left(1+\frac{dh_w}{dr_w}\right)\left(\frac{dh_t}{dr_w}\left(1+\frac{h_w}{r_w}+\frac{h_t}{r_w}\right)+\frac{h_t}{r_w}\left(1+\frac{dh_w}{dr_w}\right)\right)+$$

$$\left(\frac{h_t}{2}\frac{d^2 h_w}{dr_w^2}\right)\left(\frac{h_t}{r_w}+2\left(1+\frac{h_w}{r_w}\right)\right)$$

$$\Psi_{t2}\triangleq\frac{h_t}{r_w}\left(1+\frac{dh_w}{dr_w}\right)\left(\frac{h_t}{r_w}+2\left(1+\frac{h_w}{r_w}\right)\right)$$

$$\Psi_{w1}\triangleq\frac{dh_w}{dr_w}\left(1+\frac{h_w}{r_w}\right)+\frac{h_w}{r_w}$$

$$\Psi_{w2}\triangleq\frac{h_w}{r_w}\left(2+\frac{h_w}{r_w}\right)$$

The following is Derivation 3:

Using Derivation 2 and FIGS. 4C and 4D, we write a force balance, and derive the relationship between various pressures in the arm and cuff.

Force balance:

$$F+F_{shw}+F_{sht}=F_c+F_w+F_t$$

where $$F=Pr_w\delta l$$

$$F_c=P_c(r_w+h_w+h_w+h_t)\delta l$$

$$F_{shx}=F_{shx}(l+\delta l)-F_{shx}(l)$$

$$\delta lF_x=\sigma_x h_x\delta l$$

and x is either t or w.

As $\delta l \to 0$, $$Pr_w+\frac{dF_{shw}}{dl}+\frac{dF_{sht}}{dl}=P_c(r_w+h_w+h_t)+\sigma_w h_w+\sigma_t h_t$$

$$P+P_{sh}=P_c+P_{c,ex}+P_t$$

where $$P_{c,ex}\triangleq P_c\left(\frac{h_w}{r_w}+\frac{h_t}{r_w}\right)$$

$$P_t\triangleq\sigma_w\frac{h_w}{r_w}+\sigma_t\frac{h_t}{r_w}$$

$$P_{sh}\triangleq\frac{1}{r_w}\frac{dF_{shw}}{dl}+\frac{1}{r_w}\frac{dF_{sht}}{dl}$$

$$=\frac{r_w}{2}\frac{d^2 r_w}{dl^2}\mu_{sh2}+\left(\frac{dr_w}{dl}\right)^2\mu_{sh1}$$

$$=\frac{d^2 A}{dl^2}\left(\frac{\mu_{sh2}}{4\pi}\right)+\frac{1}{A}\left(\frac{dA}{dl}\right)^2\left(\frac{\mu_{sh1}-\mu_{sh2}}{4\pi}\right)$$

$$\mu_{shi}\triangleq\mu_w\Psi_{wi}+\mu_t\Psi_{ti}$$

The following is Derivation 4:

Here we computes simplified expressions for the terms that appear in the coefficients in Derivation 2.

$$\lambda_x\triangleq\frac{A_x}{A}$$

$$\frac{h_w}{r_w}=(1+\lambda_w)^{\frac{1}{2}}-1$$

$$\frac{dh_w}{dr_w}=(1+\lambda_w)^{-\frac{1}{2}}-1$$

$$\frac{h_t}{r_w}=(1+\lambda_w+\lambda_t)^{\frac{1}{2}}-(1+\lambda_w)^{\frac{1}{2}}$$

$$\frac{dh_t}{dr_w}=(1+\lambda_w+\lambda_t)^{-\frac{1}{2}}-(1+\lambda_w)^{-\frac{1}{2}}$$

$$\frac{d^2 h_w}{dr_w^2}h_t=\lambda_w(1+\lambda_w)^{-\frac{3}{2}}\left\{(1+\lambda_w+\lambda_t)^{\frac{1}{2}}-(1+\lambda_w)^{\frac{1}{2}}\right\}$$

The following is Derivation 5:

Here we uses Derivations 2 and 4 to estimate the value of the geometric coefficients based on the assumptions that the ratio $h_w/r_w$ is always approximately 0.06, and the ratio $h_t/r_w$ is always approximately 10.

$$\frac{h_w}{r_w}\approx 0.06 \Rightarrow \lambda_w\approx 0.12, \frac{h_t}{r_w}\approx 10 \Rightarrow \lambda_t\approx 0.12,$$

$$\frac{dh_t}{dr_w}\approx 0.85, \frac{dh_w}{dr_w}\approx -0.06, \frac{d^2 h_w}{dr_w^2}h_t\approx 0.1,$$

$$\psi_{w1}\approx 1.06, \psi_{w2}\approx 0.124, \psi_{t1}\approx 20, \psi_{t2}\approx 222$$

Derivation 6:

When we measure $$C=\frac{dV}{dP_{TR}},$$

the volume change is due not only to $P_{TR}$, but to $P_{sh}$ as well. We want to know what fraction of the total volume change is due only to $P_{TR}$. Normally we are computing the total volume change in the cuff or artery (dV dV$_{tot}$). We will find a correction factor to convert to the desired $$\frac{dV_{TR}}{dP_{TR}}.$$

$$\frac{dV_{TR}}{dP_{TR}}=\frac{dV_{tot}}{dP_{TR}}\left(\frac{dV_{TR}/dt}{dV_{tot}/dt}\right)=\kappa\frac{dV_{tot}}{dP_{TR}}.$$

$$V_{tot}=\int A(x,t)dx, V_{TR}=LA(0,t)$$

where L is the cuff length.

Letting $r_w$ refer to $r_w(0,t)$, $$\frac{dV_{tot}}{dt}=\int\frac{d}{dt}A(x,t)dx$$

$$=\int\left\{\frac{dr_w}{dt}\frac{d}{dr_w}A(x,t)+\frac{d\alpha_2}{dt}\frac{d}{d\alpha_2}A(x,t)\right\}dx$$

$$=\frac{dr_w}{dt}\int\frac{d}{dr_w}A(x,t)dx+\frac{d\alpha_2}{dt}\int\frac{d}{d\alpha_2}A(x,t)dx,$$

-continued $$\frac{dV_{TR}}{dt} = L\frac{d}{dt}A(0,t)$$
$$= L\left\{\frac{dr_w}{dt}\frac{d}{dr_w}A(0,t) + \frac{d\alpha_2}{dt}\frac{d}{d\alpha_2}A(0,t)\right\},$$

$$\frac{1}{\kappa} \triangleq \frac{dV_{tot}/dt}{dV_{TR}/dt}$$
$$= \frac{\frac{dr_w}{dt}\int \frac{d}{dr_w}A(x,t)dx + \frac{d\alpha_2}{dt}\int \frac{d}{d\alpha_2}A(x,t)dx}{L\left\{\frac{dr_w}{dt}\frac{d}{dr_w}A(0,t) + \frac{d\alpha_2}{dt}\frac{d}{d\alpha_2}A(0,t)\right\}}$$
$$= \frac{1}{L}\frac{\int \frac{d}{dr_w}A(x,t)dx + \frac{d\alpha_2}{dr_w}\int \frac{d}{d\alpha_2}A(x,t)dx}{\frac{d}{dr_w}A(0,t) + \frac{d\alpha_2}{dr_w}\frac{d}{d\alpha_2}A(0,t)}$$

We can find a model for $A(x)$ by solving the nonlinear ODE from Derivation 3.

$$P_{sh} = \frac{d^2A}{dx^2}\left(\frac{\mu_{sh2}}{4\pi}\right) + \frac{1}{A}\left(\frac{dA}{dx}\right)^2\left(\frac{\mu_{sh1} - \mu_{sh2}}{4\pi}\right)$$
$$= P_c\left(\frac{h_t + h_w}{r_w}\right) + P_t - P_{TR}$$

or $$\frac{d^2A}{dx^2} + \frac{1}{A}\left(\frac{dA}{dx}\right)^2\alpha_1 = \alpha_2$$

where $$\alpha_1 \triangleq \frac{\mu_{sh1}}{\mu_{sh2}} - 1 = \frac{\psi_{w1} + \psi_{t1}(\mu_t/\mu_w)}{\psi_{w2} + \psi_{t2}(\mu_t/\mu_w)} - 1,$$

$$\alpha_2 \triangleq \frac{4\pi}{\mu_{sh2}}P_{sh} = \frac{4\pi}{\mu_{sh2}}\left(P_c\left(\frac{h_t + h_w}{r_w}\right) + P_t - P_{TR}\right)$$

Assume that wall and tissue properties are similar and use Derivation 5. Also use $\mu_w = 137$ kPa $= 1027.6$ mmHg (from Deng et. al., American Journal of Physiology. 266(1 Pt 2):H1-10, 1994 Jan). We get $$\mu_t \approx \mu_w \approx 1027.6 \text{ mmHg},$$

$$\sigma_t \approx \sigma_w \approx P\frac{r_w}{h_w} \approx \frac{1}{0.06}P,$$

and $$\alpha_1 \approx -0.905 \approx -1,$$

$$\alpha_1 \approx -0.905 \approx -1,$$

$$\alpha_2 \approx \frac{0.0566}{1027.6}\text{mmHg}^{-1}\left(10.06\left(P_c + \frac{1}{0.06}P\right) - P_{TR}\right)$$
$$\approx 10^{-3}\text{mmHg}^{-1}(9.18P + 0.609P_c)$$

Substituting $\alpha_1$, $$\alpha_2 = \frac{d^2A}{dx^2} - \frac{1}{A}\left(\frac{dA}{dx}\right)^2 = A\frac{d^2}{dx^2}\log(A).$$

Solving for $A(x)$ and centering around $x_0 = 0$, and taking $r_w$ to mean $r(0, t)$, we get $$A(x) = A_w \cosh^2\left(\frac{\beta}{2}\eta\right),$$

$$\eta \triangleq \frac{x - x_0}{r_w}, \beta \triangleq \sqrt{\frac{2}{\pi}\alpha_2}$$

Next we evaluate each of the terms in κ:

$$\frac{d}{dr_w}A(x,t) = \pi r_w\left\{\left(1 + \cosh\left(\frac{\beta}{r_w}x\right)\right) - \frac{1}{2}\frac{\beta}{r_w}x\sinh\left(\frac{\beta}{r_w}x\right)\right\}$$

$$\frac{d}{dr_w}A(0,t) = 2\pi r_w$$

$$\frac{d}{d\alpha_2}A(x,t) = \frac{1}{2}\frac{r_w}{\beta}x\sinh\left(\frac{\beta}{r_w}x\right)$$

$$\frac{d}{d\alpha_2}A(0,t) = 0$$

$$\int \frac{d}{dr_w}A(x,t)dx = \frac{\pi}{2}r_w\{2(x_H - x_L) + 3D_2 - D_1\}$$

$$\int \frac{d}{d\alpha_2}A(x,t)dx = \frac{1}{2}\left(\frac{r_w}{\beta}\right)^2(D_1 - D_2)$$

where $x_L \triangleq 0, x_H \triangleq L/2$ $$D_1 \triangleq x_H\cosh\left(x_H\frac{\beta}{r_w}\right) - x_L\cosh\left(x_L\frac{\beta}{r_w}\right) = \frac{L}{2}\cosh\left(\frac{L}{2}\frac{\beta}{r_w}\right)$$

$$D_2 \triangleq \frac{r_w}{\beta}\left\{\sinh\left(x_H\frac{\beta}{r_w}\right) - \sinh\left(x_L\frac{\beta}{r_w}\right)\right\} = \frac{r_w}{\beta}\sinh\left(\frac{L}{2}\frac{\beta}{r_w}\right).$$

Substituting back into $\kappa$; we get $$\frac{1}{\kappa} = \frac{1}{L}\frac{\frac{\pi}{2}r_w\{2(x_H - x_L) + 3D_2 - D_1\} + \frac{d\alpha_2}{d\alpha_w}\frac{1}{2}\left(\frac{r_w}{\beta}\right)^2(D_1 - D_2)}{2\pi r_w}$$

$$= \frac{1}{4L}\left\{2(x_H - x_L) + 3D_2 - D_1\} + \frac{d\alpha_2}{dr_w}\frac{1}{\pi r_w}\left(\frac{r_w}{\beta}\right)^2(D_1 - D_2)\right\}$$

$$= \frac{1}{4L}\left\{2(x_H - x_L + D_2) + (D_2 - D_1)\left(1 + \left(\frac{1}{\pi r_w}\frac{d\alpha_2}{dr_w}\right)\left(\frac{r_w}{\beta}\right)^2\right)\right\}$$

$$= \frac{1}{4L}\left\{2(x_H - x_L + D_2) + (D_2 - D_1)\left(1 + \frac{1}{2}\frac{d\log(\alpha_2)}{d\log(r_w)}\right)\right\}$$

$$= \frac{1}{4L}\left\{2(x_H - x_L + D_2) + (D_2 - D_2)\left(1 + \frac{1}{2}S\right)\right\}$$

$$S \triangleq \frac{d\log(\alpha_2)}{d\log(r_w)} = \frac{d\log(P_{sh})}{d\log(r_w)}$$

$$\beta^2 = \frac{2\alpha_2}{\pi}$$

$$\sim 10^{-6}\text{mmHg}^{-1}(387P_c + 5842P)$$

To estimate $r_w$ we could use 0.25 cm, or choose sigmoid model (like arctangent) with pressure as is sometimes used. Here, for example, we use a logistic curve $$\left(logistic(x) = \frac{1}{1 + e^{-x}}\right).$$

$$\tilde{r_w} \sim r_{w,\min} + (r_{w,\max} - r_{w,\min})\, logistic\left(\frac{P_{TR} - P_{TR,1/2}}{\sigma}\right)$$

$$\sim (0.5 \text{ cm}) \, logistic\left(\frac{P_{TR} - 40 \text{ mmHg}}{20 \text{ mmHg}}\right)$$

In one embodiment, the Third Embodiment uses the following procedure:
1. Calculate P. $P_c$, $P_{TR}$, and C for second embodiment.
2. Calculate $r_w$ using $P_{TR}$ and the sigmoid model.
3. Calculate $\beta$ using $P_c$ and P.
4. Calculate S by numerically differentiating $\log\beta^2$ with respect to $\log r_w$ and multiplying the result by $$\frac{r_w}{\beta^2}.$$

5. Calculate $D_1$ and D2 from $$\frac{\beta}{r_w}.$$

6. Calculate κ from $D_1$, $D_2$, and S.
7. Calculate $C_{corrected} = \kappa C$.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for computerized calculation of a variable physiological parameter of a patient, the method comprising:
   (a) identifying the physiological parameter to be quantitatively monitored and estimated;
   (b) measuring an oscillometric blood-pressure signal and a tonometric blood-pressure signal, which signals are quantitatively dependent on a particular value for the physiological parameter;
   (c) obtaining a sequence of values that are based on the oscillometric signal and the tonometric signal;
   (d) receiving the sequence of values as input signals to a computer system;
   (e) processing the input signals within the computer system to convert the sequence of values to an output signal corresponding to the particular value of the physiological parameter; and
   (f) using the oscillometric signal to calibrate the tonometric signal; wherein a calibrated radial pressure waveform $P_r(t)$ is derived from the tonometric signal $S_r(t)$ as follows:

$$P_r(t) = (1/a_r)(S_r(t) - b_r) + p$$

where
   $a_r = (S_r(t_D) - S_r(t_M))/(DBP - MBP)$,
   $b_r = S_r(t_M) - a_r \text{ MBP}$, and
   $p = \rho$ gh are calibration factors, and where
   ρ=density of blood,
   g=acceleration to gravity,
   h=height difference between the oscillometric and the tonometric measurement sites, and is zero if the patient is supine,
   MBP is oscillometric mean arterial blood pressure measured near time $t_M$, and
   DBP is oscillometric diastolic blood pressure measured near time $t_D$.

2. The method of claim 1, further comprising:
   (g) calculating a first compliance value based on the calibrated radial pressure waveform;
   (h) estimating end-effects of the oscillometric signal; and
   (i) correcting the first compliance value using the estimated end effects.

3. The method of claim 1, further comprising:
   (g) calculating a first compliance value based on the calibrated radial pressure waveform.

4. A method for computerized calculation of a variable physiological parameter of a patient, the method comprising:
   (a) identifying the physiological parameter to be quantitatively monitored and estimated;
   (b) measuring an oscillometric signal and a tonometric physiological signal, which signals are quantitatively dependent on a particular value for the physiological parameter;
   (c) obtaining a sequence of values that are based on the oscillometric signal and the tonometric signal;
   (d) receiving the sequence of values as input signals to a computer system; and
   (e) processing the input signals within the computer system to convert the sequence of values to an output signal corresponding to the particular value of the physiological parameter;
   wherein the processing function (e) includes estimating a first compliance value using a compliance pressure curve.

5. The method of claim 4, further comprising:
   (f) using the oscillometric signal to calibrate the tonometric signal.

6. The method of claim 4, further comprising:
   (f) using the oscillometric signal to calibrate the tonometric signal; wherein two points along the oscillometric signal defining a subportion of the oscillometric pressure range are used with two corresponding points along the tonometric signal to calibrate the tonometric signal.

7. The method of claim 6, wherein the two points along the oscillometric signal correspond to a diastolic blood pressure and a mean blood pressure.

8. The method of claim 6, wherein the two points along the oscillometric signal correspond to a systolic blood pressure and a mean blood pressure.

9. The method of claim 4, further comprising:
   (f) using the oscillometric signal to calibrate the tonometric signal; wherein a calibrated radial pressure waveform $P_r(t)$ is derived from the tonometric signal $S_r(t)$ as follows:

$$P_r(t) = (1/a_r)(S_r(t) - b_r) + p$$

where
   $a_r = (S_r(t_D) - S_r(t_M))/(DBP - MBP)$,
   $b_r = S_r(t_M) - a_r \text{ MBP}$, and
   $p = \rho$ gh are calibration factors, and where
   ρ=density of blood,
   g=acceleration to gravity,
   h=height difference between the oscillometric and the tonometric measurement sites, and is zero if the patient is suprine,
   MBP is oscillometric mean arterial blood pressure measured near time $t_M$, and DBP is oscillometric diastolic blood pressure measured near time $t_D$.

10. A method for computerized calculation of a variable physiological parameter of a patient, p=pgh are calibration factors, and wherethe method comprising:
p=density of blood,
   (a) identifying the physiological parameter to be quantitatively monitored and estimated;
   g=acceleration to gravity,
   (b) measuring an oscillometric signal and a tonometric physiological signal, which
      h=height difference between the oscillometric and the tonometricsignals are quantitatively dependent on a particular value for the physiological parameter; measurement sites, and is zero if the patient is supine,
   (c) obtaining a sequence of values that are based on the oscillometric signal and the tonometric signal;
   (d) receiving the sequence of values as input signals to a computer system;
   (e) processing the input signals within the computer system to convert the sequence of values to an output signal corresponding to the particular value of the physiological parameter; and
   (f) using a tonometric signal to calibrate oscillometric pressure signals in a contralateral arterial site.

11. A method for computerized calculation of a variable physiological parameter of a patient, the method comprising:
   (a) identifying the physiological parameter to be quantitatively monitored and estimated;
   (b) measuring an oscillometric signal and a tonometric physiological signal, which signals are quantitatively dependent on a particular value for the physiological parameter;
   (c) obtaining a sequence of values that are based on the oscillometric signal and the tonometric signal;
   (d) receiving the sequence of values as input signals to a computer system;
   (e) processing the input signals within the computer system to convert the sequence of values to an output signal corresponding to the particular value of the physiological parameter; and
   (f) estimating end-effects of oscillometric sensor apparatus on the oscillometric signal.

12. The method of claim 11, further comprising:
   (g) using an oscillometric signal to calibrate tonometric pressure signals in a contralateral arterial site.

13. The method of claim 11, further comprising:
   (g) using the oscillometric signal to calibrate tonometric pressure; and
   (h) calculating a value for the physiological parameter.

14. The method of claim 13, wherein the physiological parameter to be estimated is compliance, the method further comprising:
   (i) calculating a first compliance value based on the calibrated tonometric pressure waveform; and
   (j) correcting the first compliance value using the estimated end effects.

15. The method of claim 11, further comprising:
   (g) using the oscillometric signal to calibrate tonometric pressure; wherein two points along the oscillometric signal defining a subportion of a oscillometric pressure range are used with two corresponding points along the tonometric signal to calibrate the tonometric signal; and
   (h) calculating a value for the physiological parameter.

16. The method of claim 15, wherein the two points along the oscillometric signal correspond to a diastolic blood pressure and a mean blood pressure.

17. The method of claim 11, further comprising:
   (g) using the oscillometric signal to calibrate the tonometric signal; wherein a calibrated radial pressure waveform $P_r(t)$ is derived from the tonometric signal $S_r(t)$ as follows:

$$P_r(t)=(1/a_r)(S_r(t)-b_r)+p$$

where
   $a_r=(S_r(t_D)-S_r(t_M))/(DBP-MBP)$,
   $b_r=S_r(t_M)-a_r$ MBP, and
   p=ρ gh are calibration factors, and where
      ρ=density of blood,
      g=acceleration to gravity,
      h=height difference between the oscillometric and the tonometric measurement sites, and is zero if the patient is supine,
      MBP is oscillometric mean arterial blood pressure measured near time $t_M$, and
      DBP is oscillometric diastolic blood pressure measured near time $t_D$; and
   (h) calculating a value for the physiological parameter.

18. The method of claim 17, wherein the physiological parameter to be estimated is compliance, the method further comprising:
   (i) calculating a first compliance value based on the calibrated tonometric pressure waveform; and
   (j) correcting the first compliance value using the estimated end effects.

19. A method for computerized calculation of a variable physiological parameter of a patient, the method comprising:
   (a) identifying the physiological parameter to be quantitatively monitored and estimated;
   (b) coupling at least a first sensor and a second sensor to the patient, the first sensor and the second sensor each being responsive to monitor different time-varying physiological waveforms, which waveforms are quantitatively dependent on a particular value for the physiological parameter;
   (c) obtaining a time-correlated dual sequence of digital values that are based on the waveforms monitored by the first and second sensors;
   (d) receiving the sequence of digital values as input signals to a computer system; and
   (e) processing the input signals within the computer system to convert the time-correlated dual sequence of digital values to an output signal corresponding to a value of the physiological parameter, wherein the physiological parameter is vascular compliance, the first sensor monitors an oscillometric waveform, and the second sensor monitors a tonometric waveform.

20. The method of claim 19, further comprising:
   (f) using an oscillometric signal to calibrate tonometric pressure; wherein two points along the oscillometric signal defining a subportion of the oscillometric pressure range are used with two corresponding points along the tonometric signal to calibrate the tonometric signal.

21. The method of claim 20, wherein the two points along the oscillometric signal correspond to a diastolic blood pressure and a mean blood presure.

22. The method of claim 20, wherein the two points along the oscillometric signal correspond to a systolic blood pressure and a mean blood pressure.

23. The method of claim 19, further comprising:
(f) using the oscillometric waveform to calibrate tonometric waveform; wherein a calibrated radial pressure waveform $P_r(t)$ is derived from the tonometric waveform $S_r(t)$ as follows:

$$P_r(t)=(1/a_r)(S_r(t)-b_r)+p$$

where
$a_r=(S_r(t_D)-S_r(t_M))/(DBP-MBP)$,
$b_r=S_r(t_{M)-ar}$ MBP, and
$p=\rho$ gh are calibration factors, and where
$\rho$=density of blood,
g=acceleration to gravity,
h=height difference between the oscillometric and the tonometric measurement sites, and is zero if the patient is supine,
MBP is oscillometric mean arterial blood pressure measured near time $t_M$, and
DBP is oscillometric diastolic blood pressure measured near time $t_D$.

24. The method of claim 19, where the (e) processing of the input signals includes estimating a first compliance value using a compliance pressure curve.

25. The method of claim 19, further comprising:
(f) estimating end-effects of oscillometric sensor apparatus on the oscillometric signal.

26. The method of claim 25, wherein the physiological parameter to be estimated is compliance, the method further comprising:
(g) using an oscillometric signal to calibrate tonometric pressure; wherein two points along the oscillometric signal defining a subportion of the oscillometric pressure range are used with two corresponding points along the tonometric signal to generate a calibrated tonometric signal;
(h) calculating a first compliance value based on the calibrated tonometric pressure waveform; and
(i) correcting the first compliance value using the estimated end effects.

27. A method for computerized calculation of a variable physiological parameter of a patient, the method comprising:
(a) identifying the physiological parameter to be quantitatively monitored and estimated;
(b) coupling at least a first sensor and a second sensor to the patient, the first sensor and the second sensor each being responsive to monitor different time-varying physiological waveforms, which waveforms are quantitatively dependent on a particular value for the physiological parameter;
(c) obtaining a time-correlated dual sequence of digital values that are based on the waveforms monitored by the first and second sensors;
(d) receiving the sequence of digital values as input signals to a computer system; and
(e) processing the input signals within the computer system to convert the time-correlated dual sequence of digital values to an output signal corresponding to a value of the physiological parameter wherein the physiological parameter is vascular compliance, the first sensor monitors an oscillometric waveform derived from oscillometric signals of a brachial artery site, and the second sensor monitors a tonometric waveform derived from tonometric signals of a contralateral radial artery site.

28. The method of claim 27, further comprising:
(f) using an oscillometric signal to calibrate tonometric pressure; wherein two points along the oscillometric signal defining a subportion of the oscillometric pressure range are used with two corresponding points along the tonometric signal to calibrate the tonometric signal.

29. The method of claim 28, wherein the two points along the oscillometric signal correspond to a diastolic blood pressure and a mean blood pressure.

30. The method of claim 28, wherein the two points along the oscillometric signal correspond to a systolic blood pressure and a mean blood pressure.

31. The method of claim 27, further comprising:
(f) using the oscillometric waveform to calibrate the tonometric waveform; wherein a calibrated radial pressure waveform $P_r(t)$ is derived from the tonometric waveform $S_r(t)$ as follows:

$$P_r(t)=(1/a_r)(S_r(t)-b_r)+p$$

where
$a_r=(S_r(t_D)-S_r(t_M))/(DBP-MBP)$,
$b_r=S_r(t_{M)-ar}$ MBP, and
$p=\rho$ gh are calibration factors, and where
$\rho$=density of blood,
g=acceleration to gravity,
h=height difference between the oscillometric and the tonometric measurement sites, and is zero if the patient is supine,
MBP is oscillometric mean arterial blood pressure measured near time $t_M$, and
DBP is oscillometric diastolic blood pressure measured near time $t_D$.

32. The method of claim 27, where the (e) processing of the input signals includes estimating a first compliance value using a compliance pressure curve.

33. The method of claim 27, further comprising:
(f) estimating end-effects of oscillometric sensor apparatus on the oscillometric signal.

34. The method of claim 33, wherein the physiological parameter to be estimated is compliance, the method further comprising:
(g) using an oscillometric signal to calibrate tonometric pressure; wherein two points along the oscillometric signal defining a subportion of the oscillometric pressure range are used with two corresponding points along the tonometric signal to generate a calibrated tonometric signal;
(h) calculating a first compliance value based on the calibrated tonometric pressure waveform; and
(i) correcting the first compliance value using the estimated end effects.

35. A system for computerized calculation of a variable physiological parameter of a patient, the system comprising:
a first sensor that measures an oscillometric blood-pressure signal that is quantitatively dependent on a particular value for the physiological parameter;
a second sensor that measures a tonometric blood-pressure signal that is quantitatively dependent on the particular value for the physiological parameter;

a first analog-to-digital converter, operatively coupled to the first sensor, that generates a first sequence of digital values that are based on the oscillometric signal;

a second analog-to-digital converter, operatively coupled to the second sensor, that generates a second sequence of digital values that are based on the tonometric signal; and a computer system, operatively coupled to the first and second analog-to-digital converters, wherein the computer system processes the first and second sequences of values to generate an output signal corresponding to the particular value of the physiological parameter, and the computer uses the oscillometric signal to calibrate the tonometric signal, and wherein a calibrated radial pressure waveform $P_r(t)$ is derived from the tonometric signal $S_r(t)$ as follows:

$$P_r(t)=(1/a_r)(S_r(t)-b_r)+p$$

where
$a_r=(S_r(t_D)-S_r(t_M))/(DBP-MBP)$,
$b_r=S_r(t_M)-a_r$ MBP, and
$p=\rho$ gh are calibration factors, and where
$\rho$=density of blood,
g=acceleration to gravity,
h=height difference between the oscillometric and the tonometric measurement sites, and is zero if the patient is supine,
MBP is oscillometric mean arterial blood pressure measured near time $t_M$, and
DBP is oscillometric diastolic blood pressure measured near time $t_D$.

36. The system of claim 35, wherein the computer system further calculates a first compliance value based on the calibrated radial pressure waveform, estimates end-effects of the oscillometric signal, and corrects the first compliance value using the estimated end effects.

37. A system for computerized calculation of a variable physiological parameter of a patient, the system comprising:

a first sensor that measures an oscillometric physiological signal that is quantitatively dependent on a particular value for the physiological parameter;

a second sensor that measures a tonometric physiological signal that is quantitatively dependent on the particular value for the physiological parameter;

a first analog-to-digital converter, operatively coupled to the first sensor, that generates a first sequence of digital values that are based on the oscillometric signal;

a second analog-to-digital converter, operatively coupled to the second sensor, that generates a second sequence of digital values that are based on the tonometric signal; and a computer system, operatively coupled to the first and second analog-to-digital converters, wherein the computer system processes the first and second sequences of values to generate an output signal corresponding to the particular value of the physiological parameter, wherein the computer system further estimates a first compliance value using;a compliance pressure curve.

38. The system of claim 37, wherein the first sensor senses the oscillometric signal from one side of a patient, the second sensor senses the tonometric signal from a contralateral arterial site, and the computer uses the oscillometric signal to calibrate tonometric pressure signals in the contralateral arterial site.

39. The system of claim 37, wherein the oscillometric physiological signal is an oscillometric blood pressure signal, the tonometric physiological signal is a tonometric blood pressure signal, and the computer system further calibrates the tonometric pressure signal based on the oscillometric pressure signal.

40. The system of claim 37, wherein the oscillometric physiological signal is an oscillometric blood pressure signal, the tonometric physiological signal is a tonometric blood pressure signal, and the computer system further calibrates the tonometric blood pressure signal with the oscillometric blood pressure signal, and wherein two points along the oscillometric signal that define a subportion of a osillometric pressure range are used with two corresponding points along the tonometric signal to calibrate the tonometric signal.

41. The system of claim 40, wherein the two points along the oscillometric signal correspond to a diastolic blood pressure and a mean blood pressure.

42. The system of claim 40, wherein the two points along the oscillometric signal correspond to a systolic blood pressure and a mean blood pressure.

43. The system of claim 37, wherein the computer system further calibrates the tonometric blood pressure signal with the oscillometric blood pressure signal; wherein a calibrated radial pressure waveform $P_r(t)$ is derived from the tonometric signal $S_r(t)$ as follows:

$$P_r(t)=(1/a_r)(S_r(t)-b_r)+p$$

where
$a_r=(S_r(t_D)-S_r(t_M))/(DBP-MBP)$,
$b_r=S_r(t_M)-a_r$ MBP, and
$p=\rho$ gh are calibration factors, and where
$\rho$=density of blood,
g=acceleration to gravity,
h=height difference between the oscillometric and the tonometric measurement sites, and is zero if the patient is supine,
MBP is oscillometric mean arterial blood pressure measured near time $t_M$, and
DBP is oscillometric diastolic blood pressure measured near time $t_D$.

44. A system for computerized calculation of a variable physiological parameter of a patient, the system comprising:

a first sensor that measures an oscillometric physiological signal that is quantitatively dependent on a particular value for the physiological parameter;

a second sensor that measures a tonometric physiological signal that is quantitatively dependent on the particular value for the physiological parameter;

a first analog-to-digital converter, operatively coupled to the first sensor, that generates a first sequence of digital values that are based on the oscillometric signal;

a second analog-to-digital converter, operatively coupled to the second sensor, that generates a second sequence of digital values that are based on the tonometric signal; and a computer system, operatively coupled to the first and second analog-to-digital converters, wherein the computer system processes the first and second sequences of values to generate an output signal corresponding to the particular value of the physiological parameter, wherein the computer system further uses a tonometric signal to calibrate oscillometric pressure signals in a contralateral arterial site.

45. A system for computerized calculation of a variable physiological parameter of a patient, the system comprising:

a first sensor that measures an oscillometric physiological signal that is quantitatively dependent on a particular value for the physiological parameter;

a second sensor that measures a tonometric physiological signal that is quantitatively dependent on the particular value for the physiological parameter;

a first analog-to-digital converter, operatively coupled to the first sensor, that generates a first sequence of digital values that are based on the oscillometric signal;

a second analog-to-digital converter, operatively coupled to the second sensor, that generates a second sequence of digital values that are based on the tonometric signal; and a computer system, operatively coupled to the first and second analog-to-digital converters, wherein the computer system processes the first and second sequences of values to generate an output signal corresponding to the particular value of the physiological parameter, wherein the computer system further estimates end-effects of oscillometric sensor apparatus on the oscillometric signal.

46. The system of claim 45, wherein the computer system further includes:

means for obtaining a time-correlated dual sequence of digital values that are based on the waveforms monitored by the first and second sensors; and means for processing the input signals to convert the time-correlated dual sequence of digital values to an output signal corresponding to a value of the physiological parameter.

47. The system claim 45, wherein the computer system further calibrates the tonometric blood pressure signal with the oscillometric blood pressure signal, and calculates a value for the physiological parameter based on the calibrated tonometric signal.

48. The system of claim 47, wherein the physiological parameter to be estimated is compliance, the system further calculates a first compliance value based on the calibrated tonometric pressure waveform, and corrects the first compliance value based on the estimated end effects.

49. The system of claim 45, wherein the computer system further calibrates the tonometric signal based on the oscillometric signal, where two points that define a subportion of a oscillometric pressure range are used with two corresponding points along the tonometric signal to calibrate the tonometric signal, and the computer system calculates a value for the physiological parameter.

50. The system of claim 49, wherein the two points along the oscillometric signal correspond to a diastolic blood pressure and a mean blood pressure.

51. The system of claim 14, wherein the computer system further calibrates the tonometric signal based on the oscillometric signal, and wherein a calibrated radial pressure waveform $P_r(t)$ is derived from the tonometric signal $S_r(t)$ as follows:

$$P_r(t)=(1/a_r)(S_r(t)-b_r)+p$$

where $a_r=(S_r(t_D)-S_r(t_M))/(DBP-MBP)$, $b_r=S_r(t_M)-a_r$ MBP, and p=ρ gh are calibration factors, and where ρ=density of blood, g=acceleration to gravity, h=height difference between the oscillometric and the tonometric measurement sites, and is zero if the patient is supine, MBP is oscillometric mean arterial blood pressure measured near time $t_M$, and DBP is oscillometric diastolic blood pressure measured near time $t_D$; and wherein the computer system further calculates a value for the physiological parameter.

52. The system of claim 51, wherein the physiological parameter to be estimated is compliance, wherein the computer system further calculates a first compliance value based on the calibrated tonometric pressure waveform, and corrects the first compliance value using the estimated end effects.

53. The system of claim 45, wherein the computer system further calibrates the tonometric signal based on the oscillometric signal, wherein two points along the oscillometric signal defining a subportion of the oscillometrtic pressure range are used with two corresponding points along the tonometric signal to calibrate the tonometric signal.

54. The system of claim 53, wherein the two points along the oscillometric signal correspond to a diastolic blood pressure and a mean blood pressure.

55. The system of claim 53, wherein the two points along the oscillometric signal correspond to a systolic blood pressure and a mean blood pressure.

* * * * *